US010114025B2

(12) United States Patent
John

(10) Patent No.: US 10,114,025 B2
(45) Date of Patent: Oct. 30, 2018

(54) MEANS AND METHODS FOR PRODUCING ANTI-PROTEOME ANTIBODIES AND IDENTIFYING CONSERVED UNIQUE OR DIFFERENTIALLY EXPRESSING MOLECULES OF ORGANISMS

(71) Applicant: PathoVacs, Incorporated, Ames, IA (US)

(72) Inventor: Manohar John, Ames, IA (US)

(73) Assignee: Pathovacs, Incorporated, Ames, IA (US)

( * ) Notice: Subject to any disclaimer, the term of this patent is extended or adjusted under 35 U.S.C. 154(b) by 428 days.

(21) Appl. No.: 14/827,551

(22) Filed: Aug. 17, 2015

(65) Prior Publication Data

US 2016/0077104 A1 Mar. 17, 2016

Related U.S. Application Data

(60) Provisional application No. 62/048,955, filed on Sep. 11, 2014.

(51) Int. Cl.
*G01N 33/68* (2006.01)

(52) U.S. Cl.
CPC ................................ *G01N 33/6842* (2013.01)

(58) Field of Classification Search
None
See application file for complete search history.

(56) References Cited

U.S. PATENT DOCUMENTS

2012/0263724 A1 10/2012 John et al.

OTHER PUBLICATIONS

Bussow et al (Nucleic Acids Research 26:5007-8) (Year: 1998).*
Kudva, I.T., et al, "Proteomics-Based Expression Library Screening (PELS): A Novel Method for Rapidly Defining Microbial Immunoproteomes", Mol. Cell. Proteomics, (2006), vol. 5(8), pp. 1514-1519. (http://www.mcponline.org/content/5/8/1514.long).
Kudva, I.T., et al, "Proteomics-Based Expression Library Screening (PELS): A Functional Proteomics Tool for Rapid Discovery of Immunogenic Pathogen-Specific Markers of Host Infection", Current Proteomics, (2008) vol. 5(1), pp. 1-9. (http://benthamscience.com/journals/current-proteomics/volume/5/issue/1/page/1/).
Nart, P., et al., "Mucosal Antibody Responses of Colonized Cattle to *Escherichia coli* 0157-Secreted Proteins, Flagellin, Outer Membrane Proteins and Lipopolysaccharide", FEMS Immunol. Med. Microbiol., (2008) vol. 52, pp. 59-68.
Larocque, R. C., et al., "Proteomic Analysis of Vibrio cholerae in Human Stool", Infection and Immunity, (Sep. 2008), vol. 76, No. 9, pp. 4145-4151.
Charles, R. C., et al., "Characterization of Anti-*Salmonella enterica* Serotype Typhi Antibody Responses in Bacteremic Bangladeshi Patients by an Immunoaffinity Proteomics-Based Technology", Clinical and Vaccine Immunology, (Aug. 2010), vol. 17, No. 8, pp. 1188-1195.
Notredame, C., et al., "T-Coffee: A Novel Method for Fast and Accurate Multiple Sequence Alignment", J. Mol. Biol., (2000), vol. 302, pp. 205-217.
Seenichamy, A., et al., "Production and Characterization of a Polyclonal Antibody of Anti-rLipL21-IgG Against Leptospira for Early Detection of Acute Leptospirosis", Biomed Research International, (2014), vol. 2014, Article ID 592858, 8 pages.
Novo, J. B., et al., "Generation of Polyclonal Antibodies Against Recombinant Human Glucocerebrosidase Produced in *Escherichia coli*", Mol Biotechnol, (2010), vol. 46, pp. 279-286.

* cited by examiner

*Primary Examiner* — Christopher M Gross
(74) *Attorney, Agent, or Firm* — McKee, Voorhees & Sease, PLC

(57) ABSTRACT

Disclosed are methods for identifying one or more amino acid molecules and nucleic acid molecules encoding such amino acid molecules of at least two proteomes that are conserved, unique or express at higher or lower levels in at least one of the proteomes. Expression libraries are used that produce the proteome, and in one embodiment, may produce the proteome from at least one cDNA expression library in one to five reactions. Anti-proteome antibodies are prepared that selectively bind to one of the proteomes and binding with at least one second proteome compared.

19 Claims, 12 Drawing Sheets
(6 of 12 Drawing Sheet(s) Filed in Color)

Specification includes a Sequence Listing.

Figure 3

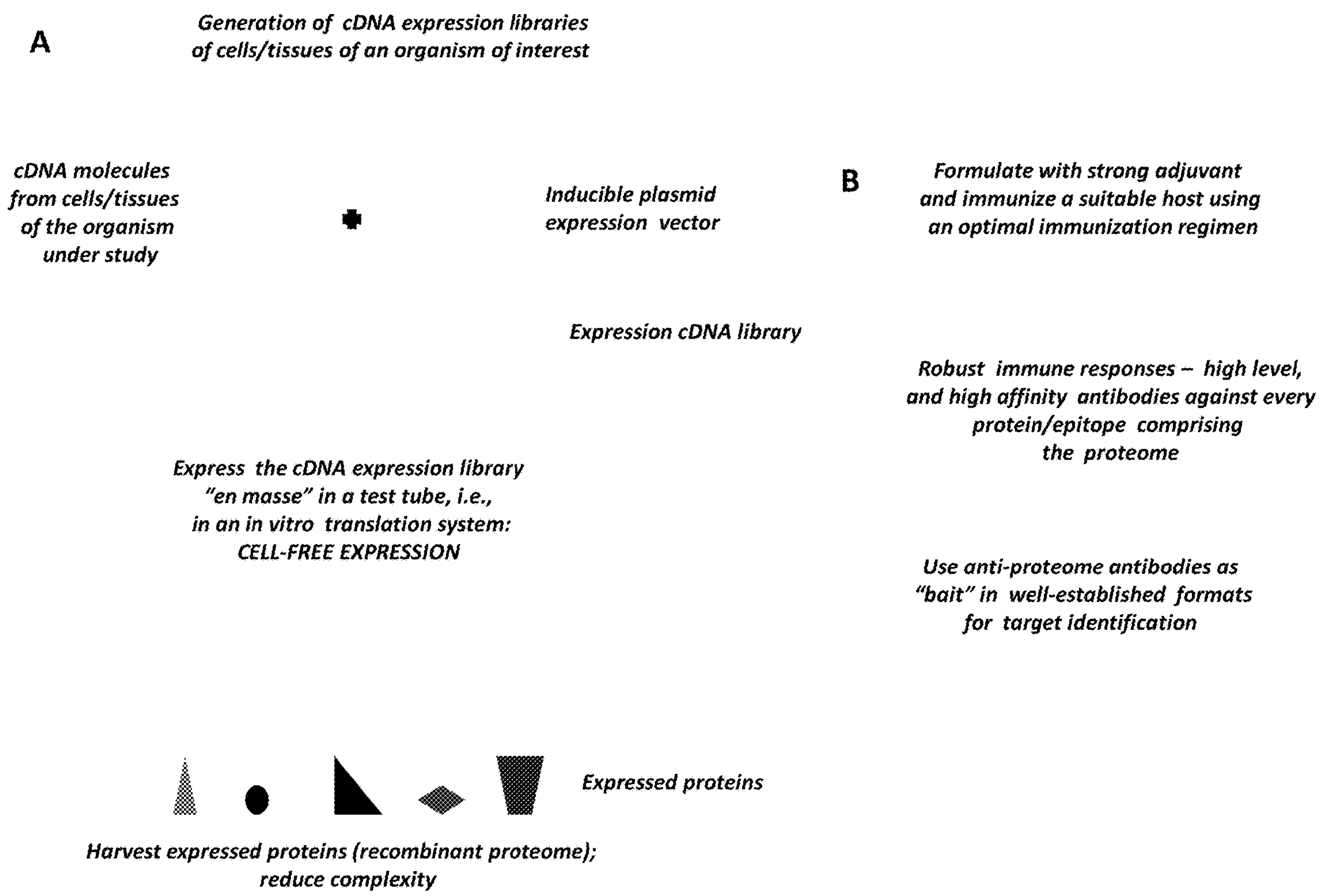

A

Generation of cDNA expression libraries of cells/tissues of an organism of interest cDNA molecules from cells/tissues of the organism under study → Inducible plasmid expression vector Expression cDNA library Express the cDNA expression library "en masse" in a test tube, i.e., in an in vitro translation system: CELL-FREE EXPRESSION Expressed proteins Harvest expressed proteins (recombinant proteome); reduce complexity

B

Formulate with strong adjuvant and immunize a suitable host using an optimal immunization regimen Robust immune responses – high level, and high affinity antibodies against every protein/epitope comprising the proteome Use anti-proteome antibodies as "bait" in well-established formats for target identification

Figure 7A

```
T-COFFEE OUTPUT

 BAD AVG GOOD

Conserved   :  36
LTB         :  87
cons        :  50

Conserved   MQFITNGPDIPDEFLQAHEEGRVVFFCGAGISYPAGLPGFKGLVELIYQRNGTTLSEIEREVFERGQFD
LTB         MNKV-----------------------------------------------------------------

cons        *: :


Conserved   GTLDLLERRLPGQRIAVRRALEKALKPKLRRRGAIDTQAALLRLARSREGALRLVTTNFDRLFHVAAKR
LTB         ---------------------------------------------------------------------

cons


Conserved   TGQAFQAYVAPMLPIPKNSRWDGLVYLHGLLPEKADDTALNRLVVTSGDFGLAYLTERWAARFVSELFR
LTB         ------KCYVL-------------------------FTAL-----------LSSLCAYGAPQSITELCS

cons             :.**                          ***           *: *    *.: ::**


Conserved   NYVVCFVGYSINDPVLRYMMDALAADRRLGEVTPQVWALGECE--PGQEHRKAIEWEAKGVTPILYTVPA
LTB         EYRNTQI-YTINDKILSY-TESMAGKRENVIITFKSGATFQVEVPGSQHID-------------------

cons        :*     : *:*** :* *  :::*..*.:   :* :   *   : * **.:* .


Conserved   GSTDHSVLHQTLHAWADTYRDGIQGKKAIVVKHALARPQDSTRQDDFVGRMLWALSDKSGLPAKRFAEL
LTB         -----------------------SQKKAIE---------------------------------------

cons                                *:*:


Conserved   NPAPPLDWLLKAFSDERFKYSDLPRFCVSPEVEIDPKLRFSLVQRPAPYELAPQMSLVSGCVSASKWDD
LTB         ---------------------------------------------------------------------
```

Figure 7B cons

Conserved VMSHIARWLVRYLGDPRLIIWIAERGGQIHDRWMFLIESELDRLAALMRERKTSELDEILLHSPLAIPG
LTB ---------------------------------------------------------------------- cons

Conserved PPMSTLWRLLLSGRVKSPLQNLDLYRWQNRLKNEGLTTTLRLELRGLLSPKVMLRRPFRYSEDDSSSTD
LTB -----------------------------RMKD-----TLRI---------------------------- cons *:*: ***:

Conserved EPLRIKQLVDNELVLTADYVRSTLFDLADESWKSSLPYLLEDFQQLLRDALDLLRELGESDDRHDRSHW
LTB ---------------------------------------------------------------------- cons

Conserved DLPSITPHWQNRGFRDWVSLIELLRDSWLAVRAKDSDQASRIAQNWFELPYPTFKRLALFAASQDNCIP
LTB ---------------------------------------------------------------------- cons

Conserved PERWVNWLLEDGSWWLWATDTRREVFRLFVLQGRHLTGIAQERLETAILAGPPREMYEDNLEADRWRYL
LTB ---------------------------------------------------------------------- cons

Conserved VAHSVWLCLAKLRGAGLVLGESAATRLTEISTAYPKWQLATNERDEFSHWMSGTGDPGFEESIDVDIAP
LTB ------------------------TYLTE----------------------------------------- cons * ***

Conserved RKNQELVQWLAKPMPERLPFYEDTWSDVCRTRFFHSLYALRKLSQDDVWFVGRWREALQTWAEPGMILR
LTB ----------------------------------------------------------------------

Figure 7C

```
cons

Conserved  SWRYAAPLVLDMPDAVLQEISHAVTWWMEEASKTILCHEKILLALCRRVLMIETSPESSTIRNGIETYD
LTB        ----------------------------------------------------------------------

cons

Conserved  PVSTAINHPIGHVTQSLITLWFKQNPNDNDLLPVELKTLFTKLCNVQIELFRHGRVLLGSRLIAFFRVD
LTB        -------------------------------------TKIDKLC--------------------------

cons                                                * : ***

Conserved  RPWTEQYLLPLFAWSNPVEAKAVWEGFLWSPRLYEPLLIAFKSDFLESANHYSDLGEHRQQFAIFLTYA
LTB        ----------------------------------------------------------------------

cons

Conserved  ALGPTEGYTVEEFRTAISALPQEGLEVAAQALYQALEGAGDQREEYWKNRVQPFWQQVWPKSRNLATPR
LTB        ----------------------------------------------VWNNRT------------------

cons                                                        *:*:.

Conserved  ISESLTRMVIAARGEFPAALAVVQDWLQPLEHLSYDVRLLLESDICSRYPADALSLLNAVIAEQHWGPR
LTB        ----------------PNSIA--------------------------------AISME------------

cons                       * ::*                                *:*:

Conserved  ELGQCLLQIVQAAPQLEQDVRYQRLNEYSRRRSV
LTB        ---------------------------------N

cons
```

Figure 8A

```
T-COFFEE OUTPUT

 BAD AVG GOOD

Conserved   MQFITNGPDIPDEFLQAHEEGRVVFFCGAGISYPAGLPGFKGLVELIYQRNGTTLSEIERRVFERGQFD
LTB         MNKVKCYVLFTALLSSLCAYG------------------------------------------------

cons        *: :.     :.  : .    *


Conserved   GILDLLERRLFGQRIAVPKALEKALAPNLRRRGAIDTQAALLRLARSREGALPLVTTNFDRLFHVAAER
LTB         ---------------------------------------------------------------------

cons


Conserved   TGQAFQAYVAPMLPIPKNSPWDGLVYLHGLLPEKADDIALNRLVVISGDFGLAYLTERWAARFVSELFR
LTB         -----------------------------------------------------------APQSITELCS

cons                                                                   *.: ::**


Conserved   NYVVCFVGISINDPVLRYMMDALAASRRLGEVIPQVWALGECEPGQEHRRAIEWEAKGVIPILYTVFAG
LTB         EYHNTQI-YTINDKILSYT-ESMAGKREMVIITFKSGAT------------------------------

cons        :*     :  *:*** :* *   ::*..*.:   :*  :   *


Conserved   STDHSVLHQTLHAWADTYRDGIQGKKAIVVKHALARPQDSTRQDDFVGRMLWALSDKSGLPAKRFAELN
LTB         ---------------------------------------------------------------------

cons


Conserved   PAPPLDWLLKAPSDERFKYSDLPRFCVSPHVEIDPKLKFSLVQRPAPYELAPQMSLVSGCVSASKWDDV
LTB         ---------------------------------------------------------------------

cons


Conserved   MSHIARWLVRYLGDPRLIIWIAERGGQIHDRWMFLIESELDRLAALMRERKTSELDEILLHSPLAIPGP
LTB         ---------------------------------------------------------------------
```

Figure 8B

```
cons

Conserved   PMSTLWRLLLSGRVKSPLQNLDLYRWQNRLKNEGLTTTLRLELRGLLSPKVMLRRFFRYSEDDSSSTDE
LTB         -----FQVEVPGSQHIDLQNLDLYRWQNRLKNEGLTTTLRLESQKKAIERM-----------------------

cons             ::: :.*  :  ************************* :     ::

Conserved   PLRIKQLVDWELVLIADYVRSTLFDLADESWKSSLPYLLEDFQQLLRDALDLLRELGESDDRHDRSHWD
LTB         ----------------------------------------------------------------------

cons

Conserved   LFSIIPHWQNRGFRDWVSLIELLRDSWLAVRAKDSDQASRIAQNWFELPYPIFKRLALFAASQDNCIPF
LTB         ----------------------------------------------------------------------

cons

Conserved   ERWVNWLLEDGSWWLWATDTRREVFRLFVLQGRHLIGIAQEELEIAILAGFPREMYEDNLEADRWHYLV
LTB         ---------------------KDTLRITY-----------------------------------------

cons                             ::.:*:

Conserved   AHSVWLCLAKLRGAGLVLGESAATPLIEISTAYPKWQLATNERDEFSHWMSGTGDPGFEESIDVDIAPR
LTB         ----------------------------------------------------------------------

cons

Conserved   KWQELVQWLAKPMPERLPFYEDTWSDVCRTPFFHSLYALRKLSQDDVWPVGRWREALQTWAEPGMILRS
LTB         ----------------------------------------------------------------------

cons

Conserved   WRYAAPLVLDMPDAVLQEISHAVTWWMEEASKTILCHEEILLALCRPVLMIETSPESSTIRNGIETYDP
LTB         ----------------------------------------------------------------------

cons

Conserved   VSTAINHPIGHVTQSLITLWFKQNPNDNDLLPVELKTLFIKLCNVQIELFRHGRVLLGSRLIAFFRVDR
LTB         ----------------------------------------------------------------------

cons
```

Figure 8C

```
Conserved   PWIEQYLLPLFAWSNPVEAKAVWEGFLWSPRLYEPLLIAFKSDFLESANHYSDLGEHRQQFAIPLTYAA
LTB         -LTETKIDKLCVWNNK-----------------------------------------------------

cons          **   :   *  .*.*

Conserved   LGPIEGYIVEEFKIAISALFQEGLEVAAQALYQALEGAGDQREEYWKNRVQPFWQQVWFKSRNLATPRI
LTB         ---------------------------------------------------------------------

cons

Conserved   SESLTRMVIAARGEFPAALAVVQDWLQPLEHLSYDVRLLLESDICSKYFADALSLLNAVIAEQHWGPRE
LTB         --------------TPNSIAAIS-------------------------------MEN------------

cons                       *  :;*.:.                              :  *

Conserved   LGQCLLQIVQAAPQLEQDVRYQRLNEYSPRRSV
LTB         ---------------------------------

cons
```

MEANS AND METHODS FOR PRODUCING ANTI-PROTEOME ANTIBODIES AND IDENTIFYING CONSERVED UNIQUE OR DIFFERENTIALLY EXPRESSING MOLECULES OF ORGANISMS

REFERENCE TO RELATED APPLICATION

This application claims priority to USSN 62/048,955, filed Sep. 11, 2014, the contents of which are incorporated herein by reference in its entirety.

STATEMENT REGARDING FEDERALLY SPONSORED RESEARCH OR DEVELOPMENT

This invention was made in part with Government support under grant number 2012-33610-19501 awarded by United States Department of Agriculture (USDA) Small Business Innovation Research. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 12, 2015, is named 250002-US_SL.txt and is 31,847 bytes in size.

BACKGROUND

The cognizance that an infectious disease can be caused by many variants of a particular infectious agent/pathogen prevalent in diverse geographical regions of the globe has resulted in a paradigm shift in regards to development of efficacious vaccine, diagnostic and therapeutic measures against such pathogens. In particular, the focus has shifted from modalities that narrowly target one particular pathogen variant (strain) that predominates in a specific geographical area to those that broadly cover all pathogen strains with disease causing potential in different parts of the globe. This paradigm shift has brought with it a set of unique challenges, especially those that pertain to the identification of pathogen components, including proteins that are "shared" by all of the variants. Because such "shared" or "conserved" proteins have potential to be the basis for development of broad management options against infectious diseases, the formulation of strategies that facilitate definition of shared/conserved pathogen proteomes (the complement of proteins encoded by the pathogen genome) is of high priority.

In this context, one approach for defining such pathogen protein components is to zero in on those that are produced by the pathogen (and its variants) when it is engaged in an actual process of infection of the host (in vivo expressed or IVE). The rationale is that a subset of IVE proteins confers on the pathogen the ability to cause disease, and hence these IVE proteins are likely to have excellent vaccine, diagnostic and therapeutic potential. Historically, a popular strategy for identification of IVE pathogen proteins has been to exploit the defense (also called the immune response, characterized by production of diverse host molecules, including antibodies) mounted by a host in response to an infection caused by a particular pathogen. This strategy is predicated on the premise that antibodies are produced against infection-relevant pathogen proteins, and hence are an apt tool for identifying IVE proteins using well-established protocols.

Despite this, antibodies produced by a host during natural infection/disease are limited and not ideal for identification of "shared/conserved" pathogen proteins. The vast majority of these "shared" proteins (or "shared" regions or "epitopes" [regions on proteins that are the actual targets of antibodies] on disparate proteins) are involved in functions that are indispensable to the pathogen, as a consequence of which they have remained unchanged (conserved) through evolution. Given their importance, pathogens have developed multiple "decoy" mechanisms, which are deployed during natural infection/disease, to either "hide" these "shared/conserved" epitopes from the host immune response (FIG. 1, Panel I) or prevent access of antibodies generated against these highly conserved proteins from reaching their cognate targets by antibodies against those pathogen epitopes/proteins that are produced by only some of the variants i.e., strain-specific and not shared/conserved (FIG. 1, Panel II; antibodies against strain-specific proteins induce excellent protection against disease with the same strain but not related strains).

SUMMARY

Methods are provided for identifying one or more amino acid and also nucleic acid molecules encoding the same of at least two proteomes of an organism that are conserved, unique, or express at higher or lower levels in at least one of the proteomes, and which in an embodiment may be used as therapeutic molecules. DNA expression libraries are created of each proteome and the proteome expressed. Anti-proteome antibodies are prepared that selectively bind to one of the proteomes and binding of the antibodies to the at least one second proteome compared. Conserved, unique or differentially expressing amino acid molecules may be identified. In further embodiments a first generated proteome may be administered with at least one adjuvant to a host to produce anti-proteome antibodies. Still further embodiments provide for producing a proteome by expressing a proteome from at least one cDNA expression library in one to five reactions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a flow chart depicting strategy for generation of anti-proteome antibodies against proteomes encoded by EcDNAlibraries.

FIG. 7A-C is an alignment of ETEC LTB sequences (SEQ ID NO: 9) and Conserved Hypothetical Protein (CHP) (SEQ ID NO: 10). Red color indicates agreement across all methods; yellow, denotes interpretation with caution; and blue/purple indicative of poor agreement/low confidence.

FIG. 8A-C is an alignment of ETEC CHP of SEQ ID NO: 11 with ETEC LTB-CHP chimeric protein (SEQ ID NO: 12). Red color indicates agreement across all methods; yellow, denotes interpretation with caution; and blue/purple indicative of poor agreement/low confidence.

DESCRIPTION

Figure 1:
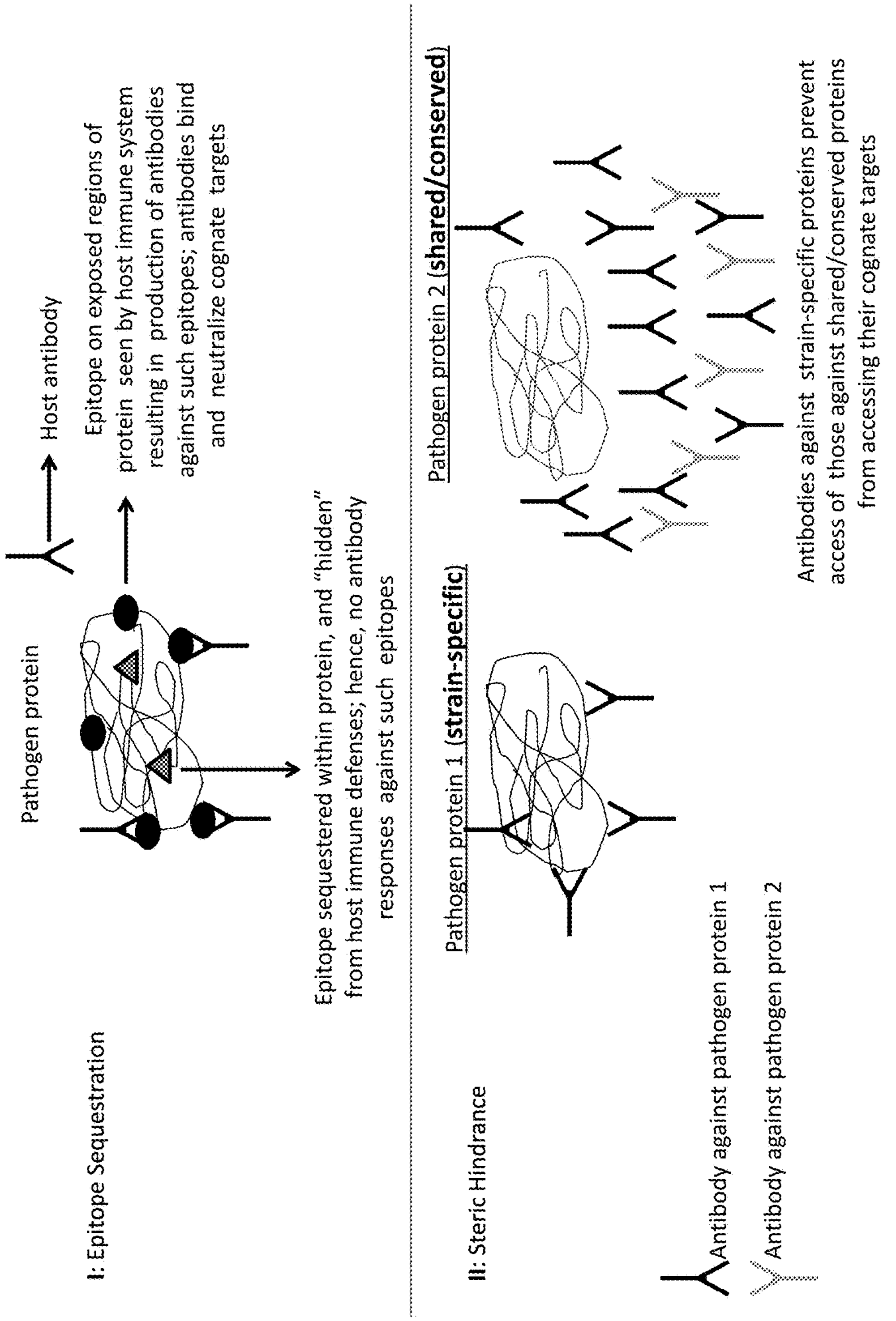
FIG. 1 is a flow chart depicting pathogen "decoy" mechanisms operating during natural infection.

As described here, antibodies from body fluids of hosts with an ongoing or recent infection are not optimal for defining "shared" or "conserved" proteins/epitopes that are the basis for development of broadly protective vaccines, diagnostics or therapeutics.

The methods here allow for production of the entire proteome of a target organism. When referring to a proteome is meant the entire complement of proteins produced by an organism, that is, the proteins specified by the genes of the organism. The proteome can be used in one embodiment to produce anti-proteome antibodies in a host. Reference made to a host refers to any convenient host production, and the precise host cell used is not critical. A molecule may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells) or viral host. Such cells are available from a wide range of sources (e.g., the American Type Culture Collection, Rockland, Md.). The method of transformation or transfection and the choice of expression vehicle will depend on the host system selected. Transformation and transfection methods are standard methods; expression vehicles may be chosen from those known in the art. By way of example without limitation, one bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein. Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

The methods described here can be used to identify conserved (also referred to as "shared") or unique amino acid molecules or differentially expressing amino acid molecules between one biotype and another, or among different unrelated organisms. Nucleic acid molecules may also be identified which encode such amino acid molecules. The amino acid or proteome of a target organism can be a sequence that is targeted for enhancement, inhibition, or identification of a particular biotype and/or function of the amino acid, such as with use as a biomarker which identifies the biotype. The target organism function in one example may be increased or decreased, and where the target is a pathogen, the identified amino acid molecules that result from the process or nucleic acid encoding them may be used as a therapeutic molecule. The target organism can be any organism which produces a proteome, whether animal, plant, virus, bacteria, fungi, or other organism or microorganism. The proteomes which may be compared to identify such molecules can be two proteomes compared to one another or more; three, four, five, six or more proteomes may be compared for the purpose of identifying such molecules.

The process can, in an embodiment, be used for identifying conserved molecules such as epitopes and proteins across proteomes of unrelated organisms. By way of illustration without intending to be limiting, it is possible to screen for universal vaccine candidates shared across different species such as pathogen species and general (such as *E. coli* and *Salmonella* by way of further example) or conserved proteins across phylogenetically distant organisms (such as mouse and humans, etc.)

The process is particularly useful in associating distinct molecules with a biotype of an organism. By referring to a biotype is meant a difference among target organisms by a particular characteristic over other members of the species. By way of example, without limitation, such pathogens may vary by variation of a DNA sequence, RNA sequences, pathogenic response, serological type, response of the exposed animal to a specific vaccine, or other variations. See Sambrook et al, Molecular Cloning: *A Laboratory Manual* Third edition, Cold Spring Harbor Laboratory, Cold Spring Harbor, N.Y. (2001); *DNA cloning A Practical Approach*, Vol. I and II, Glove, D. M. edit. IRL Press Ltd., Oxford, 1985; Harlow and Lane, *Antibodies A Laboratory Manual*, Cold Spring Harbor Publications, N. Y. 1988. As an example, influenza is a virus that is grouped into categories A, B and C based on serologic cross reactivity of internal proteins such as hemagglutinin and neuraminidase proteins. It can be distinguished by subtype and cluster. Porcine Reproductive Respiratory Virus is classified based on whether it is a European or North American strain. Glycan typing is yet another example of biotyping. See, e.g., Harris et al. US Publication No. 20130122025 incorporated herein by reference in its entirety. Any biotyping method to distinguish an organism from another of the species may be used.

As one use of the molecules that can be identified by the process, a therapeutic molecule may be produced which can be the amino acid molecule(s) so identified or a nucleic acid which encodes the amino acid. By therapeutic molecule is included a molecule that is useful in treatment of a disorder or condition, whether used for producing a protective response to an immunogenic molecule, by identifying molecules that, if inhibited, produce a desired result, such as introducing dsRNA into a cancerous cell or tumor, identifying a molecule which is required for initiation or maintenance of a disease or pathology. See, for example, Fire et al. U.S. Pat. No. 6,506,559, incorporated herein by reference in its entirety. A therapeutic molecule is one which is useful for treating a disorder, disease or condition.

The terms "protecting", "protection", "protective immunity" or "immunogenic response," as used herein, are intended to mean that the animal mounts an active immune response to the vaccine or polypeptides of the present invention, such that upon exposure to the disease challenge, the animal is able to combat the infection. The animal may or may not produce antibodies in response, but the animal will have decreased morbidity or mortality resulting from administration of the vaccine. Thus, a protective immune response will decrease the incidence of morbidity and mortality from exposure to the microorganism among a host animal. The animal will be protected from subsequent exposure to the disease-causing agent. As discussed herein, the nucleic acid molecule may be used as a probe or primer for identifying other sequences.

The processes described can, for example, be used to identify immunogenic pathogen molecules from any pathogenic organism. By way of example, without limitation, such pathogens can include bacteria, fungi, viruses, annelids, nematodes, helminths, and protozoans.

Once a polypeptide is expressed, it is isolated, e.g., using affinity chromatography. In one example, an antibody raised against a polypeptide of the invention may be attached to a column and used to isolate the recombinant polypeptide. Lysis and fractionation of polypeptide-harboring cells prior to affinity chromatography may be performed by standard methods. Once isolated, the recombinant protein can, if desired, be further purified, e.g., by high performance liquid chromatography (see, e.g., Fisher, *Laboratory Techniques, In Biochemistry And Molecular Biology*, eds., Work and Burdon, Elsevier, 1980). Polypeptides can also be produced by chemical synthesis (e.g., by the methods described in *Solid Phase Peptide Synthesis*, 2nd ed., 1984 The Pierce Chemical Co., Rockford, Ill.).

Any convenient library may be used and the production of such libraries and screening of expression libraries involves techniques well known to one skilled in the art. See, e.g., Harlow, E. and Lane, eds., 1988, *"Antibodies: A Laboratory Manual*", Cold Spring Harbor Press, Cold Spring Harbor.) The examples include illustration by use of three libraries and a pET vector, however the process need not use this system, and use of other methods of producing a library may be used which provide for a collection of the amino acids or DNA which express the amino acids of interest. One or more libraries may be used. In an embodiment three expression libraries are used which provides for differential expression of the proteins of the library, that is, by varying expression of proteins having differing optimal expression conditions, which are particularly useful with an expression library construction. A pET vector is used in the illustration, however, the process may use other systems and other vectors and expression hosts can be used. By way of example, without limitation, other vector/host systems that could be used include Gram positive expression vectors and hosts. Another system under adaptation to proteome expression is the *E. coli* CELL-FREE In Vitro Translation System that uses an *E. coli* extract containing all of the elements for protein synthesis to produce proteins in a test tube. This removes all constraints imposed by bacterial host strains, including the inability to tolerate toxic proteins, over production of proteins, and protein solubility issues. In still another example, cDNA is purified and sectioned into gel slices, in one example into five gel slices which together include the entire cDNA of the proteome. When expressed, and in a preferred embodiment when expressed in one to five reactions, the entire proteome is produced. Clearly many variations are available which can produce the proteome from a library and in an embodiment can produce from a cDNA library the proteome in one to five reactions.

The examples also illustrate the use of proteomes encoding cDNA expression libraries constructed using mRNA of cells/tissues of an organism, including a pathogen, for generation of anti-proteome antibodies. Described here is a process of developing high quality anti-proteome antibodies against the complement of proteins encoded by a cDNA expression library by starting with a proteome that is a true representation of a cDNA expression library. What this means is that every cDNA molecule represented in the library will be expressed to produce the encoded protein. Historically, proteins encoded by such cDNA libraries have been expressed via transfection of appropriate cell lines and harvesting expressed proteins following culture of such transfected cell lines. Although cell-based translation systems have been demonstrated to be effective for expression of individual recombinant cDNA molecules, wherein protein expression can be systematically monitored and conditions tweaked for optimal expression, such systems are inadequate for generating comprehensive proteomes encoded by the entire cDNA library, particularly because of "holes" in the proteome owing to lack/suboptimal expression of subsets of proteins toxic to the expression host cells that harbor the recombinant cDNA molecules, as well as proteins that are poorly soluble. To circumvent the constraints imposed by biological cell-based systems, commercially available cell-free in vitro translation systems are popular; however, such systems currently permit expression of only single/few cDNA molecules per reaction. This fact is a significant bottleneck to rapidly generating complete proteomes for downstream applications (owing to prohibitive costs and protracted time frames), especially given that expression cDNA libraries encoding comprehensive proteomes comprise thousands of recombinant individual cDNA molecules (derived from messenger RNA (mRNA) from cells/tissues of organisms, including pathogens) cloned in a plasmid expression vector. Here, a new strategy for expression of an entire cDNA library "en masse" in a test tube (in vitro/cell-free translation system) for producing the starting material (proteome) for generation of anti-proteome antibodies in an experimental host is described. The strategy presented here permits expression of an entire cDNA library in a single or few test tube-based reactions. Where previous processes to express thousands of clones from a cDNA library required several thousand such reactions and required trained personnel several months to generate large proteins and cost thousands of dollars, the approach here allows for expression of entire cDNA expression library or hundreds of clones pooled together in a single or few cell free translation reactions and requires one trained person two weeks or less to generate a representative proteome at the cost of a few thousand dollars. The use of the resultant proteome specified by components of the cDNA library for antibody production is described. An example of an application of the successful use of such anti-proteome antibodies is also described.

An embodiment provides for "en masse" expression of a cDNA library in a cell-free translation system to obtain the entire proteome. This new strategy presents a rapid and convenient strategy to generate proteomes for a variety of applications, especially for antibody production against the proteome of interest. The expression of entire cDNA libraries in one/few reactions in vitro has numerous advantages, including a significant reduction in costs and time for obtaining comprehensive proteome encoded by such libraries for diverse applications. For generation of anti-proteome antibodies, such "en masse" expressed proteins (the proteome) serve as the immunogen, which following administration to experimental hosts and in an embodiment administered along with adjuvants results in elicitation of high titer and high affinity polyclonal antibodies against every possible epitope on these proteins. To our knowledge, this is a unique approach and a first description of a strategy for expressing the entire proteome encoded by a composite cDNA library constituted by mRNA from cells/tissues of an organism in a single/few reaction(s) in a test tube for downstream applications, including generation of anti-proteome antibodies. By a single or few reactions in an embodiment is one to five reactions. By way of further example, the cDNA library can be expressed in one reaction, but it may not be economical where the cDNA is over 2000 molecule, as costs to conduct the reaction will increase. cDNA molecules over 2000 will be more economically performed in more than one reaction. In another example of an economically feasible process, up to five in vitro reactions of 300-500 molecules of cDNA per reaction may be used to produce the proteome.

By way of example without limitation, an application of anti-proteome antibodies developed in a phylogenetically distant experimental host against the proteome encoded by an expression cDNA library constructed using mRNA isolated from brains (thalamus/cortex) of healthy mice for determining proteins that are specific to thalamii of brains of mice subjected to blast-mediated traumatic brain injury (TBI; i.e., conserved in mouse brains with TBI) is described (below).

One skilled in the art recognizes that it is also possible to express pooled cDNA libraries of multiple pathogens or different tissue from the same host in a cell free translation system.

An antibody (or an immunoglobulin) is a protein synthesized by an animal in response to the presence of a foreign substance that is called an antigen. The antibody may be produced by exposing the animal to a pathogen, portion of a pathogen sequence, amino acid, and may be isolated from the pathogen and the molecule may also be synthetically produced. Further reproduction of the antibody may be achieved in other host cells and production systems. Each antibody molecule has a unique structure that enables it to bind specifically to its corresponding antigen, but all antibodies have the same overall structure. An antibody molecule is composed of two distinct regions. One is a constant region and the other is a variable region that gives an antibody the specificity to a vast variety of different antigens.

Five major classes of antibodies are IgM, IgD, IgG, IgA, and IgE. IgG is the most abundant class. IgG, as an example, has a molecular weight of 150 kDa and is composed of two different types of polypeptide chains: one is the heavy chain (50 kDa) and the other is the light chain (25 kDa). Each IgG molecule has two heavy chains and two light chains linked by disulfide bonds. Variable regions of the heavy (VH) and light (VL) chains together function as the variable region of the antibody and give the antibody the ability to bind a specific antigen.

By "specifically binds" is meant a compound or antibody which recognizes and binds a polypeptide but which does not substantially recognize and bind other molecules in a sample, for example, a biological sample, which naturally includes a polypeptide.

As to amino acid molecules/sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., *Basic Methods in Molecular Biology* Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., see, e.g., Creighton, Proteins: Structures and Molecular Properties (WH Freeman & Co.; 2nd edition (December 1993).

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with gene, cDNA, and mRNA encoded by a gene.

Unless otherwise indicated, a particular nucleic acid sequence also implicitly encompasses conservatively modified variants thereof (e.g. degenerate codon substitutions) and complementary sequences as well as the sequence explicitly indicated. The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 2001). For example, the sequence identified, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 2001).

Hybridization of such sequences may be carried out under stringent conditions. By “stringent conditions” or “stringent hybridization conditions” is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl, *Anal. Biochem.*, 138:267-284 (1984): Tm=81.5° C.+16.6 (log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of the complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (2001) and Haymes et al. (1985) In: *Nucleic Acid Hybridization, a Practical Approach*, IRL Press, Washington, D.C.

The term “substantially homologous” as used herein in connection with an amino acid or nucleic acid sequence includes sequences having at least 50%, 70% or 75%, preferably at least 80%, and even more preferably at least 85%, 90%, 95%, 96%, 97%, 98% or 99%, sequence identity to the amino acid or nucleic acid sequence disclosed or any amount in between. Substantially homologous sequences thus include single or multiple bases or amino acid alterations (additions, substitutions, insertions or deletions) to the sequences of the invention. The substantially homologous nucleic acid sequences also include nucleotide sequences that hybridize to the sequences (or their complementary sequences), e.g., hybridize to nucleotide sequences encoding one or more of the light chain or heavy chains, the light or heavy chain variable regions of the invention, or the antibodies (or hybridize to their complementary sequences), under at least moderately stringent hybridization conditions.

Binding to the same epitope/antigen can be readily tested by methods well known and described in the art, e.g., using binding assays, e.g., a competition assay. Thus, a person skilled in the art will appreciate that binding assays can be used to test whether "substantially homologous" antibodies have the same binding specificities as the antibodies and antibody fragments of the invention, for example, binding assays such as ELISA assays or Biacore assays can readily be used.

The following terms are used to describe the sequence relationships between two or more nucleic acids or polynucleotides: (a) "reference sequence", (b) "comparison window", (c) "sequence identity" and (d) "percentage of sequence identity." (a) As used herein, "reference sequence" is a defined sequence used as a basis for sequence comparison. A reference sequence may be a subset or the entirety of a specified sequence; for example, as a segment of a full length promoter sequence, or the complete promoter sequence. (b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches. Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441, as an example of the use of PILEUP); by the local homology algorithm of Smith & Waterman (Adv. Appl. Math. 2: 482 (1981)); by the homology alignment algorithm of Needleman & Wunsch (*J. Mol. Biol.* 48:443-453 (1970)); by the search for similarity method of Pearson (*Proc. Natl. Acad. Sci.* USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244; Corpet (1988), *Nucleic Acids Res.* 16:10881-10890; Huang, *Computer Applications in the Biosciences* 8:155-165 (1992); and Pearson (1994), *Methods in Mol. Biol.* 24:307-331); Pfam (Sonnhammer (1998), *Nucleic Acids Res.* 26:322-325); TreeAlign (Hein (1994), *Methods Mol. Biol.* 25:349-364); MEG-ALIGN, and SAM sequence alignment computer programs; or, by manual visual inspection.

Another example of algorithm that is suitable for determining sequence similarity is the BLAST algorithm, which is described in Altschul et al, (1990) *J. Mol. Biol.* 215: 403-410. The BLAST programs (Basic Local Alignment Search Tool) of Altschul, et al., searches under default parameters for identity to sequences contained in the BLAST "GENEMBL" database. A sequence can be analyzed for identity to all publicly available DNA sequences contained in the GENEMBL database using the BLASTN algorithm under the default parameters. Software for performing BLAST analyses is publicly available through the National Center for Biotechnology Information, www.ncbi.nlm.nih.gov/; see also Zhang (1997), *Genome Res.* 7:649-656 for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992), Proc. Natl. Acad. Sci. USA 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), *Proc. Natl. Acad. Sci. USA* 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J. Mol. Biol.* 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), Proteins 17: 49-61), which is currently the default choice for BLAST programs. BLOSUM62 uses a combination of three matrices to cover all contingencies. Altschul, *J. Mol. Biol.* 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915). (c) As used herein, "sequence identity" or "identity" in the context of two nucleic acid sequences makes reference to the residues in the two sequences that are the same when aligned for maximum correspondence over a specified comparison window. (d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

One skilled in the art readily appreciates there are many uses for an immunogenic nucleic acid molecule, as formulated as part of a vaccine, in identifying other molecules, treatment of disease to name a few applications.

EXAMPLES

The following examples are presented by way of illustration and are not intended to limit the scope of the invention. All references cited herein are incorporated herein by reference.

Host antibodies are excellent tools for determining proteins that are produced by a pathogen during the process of infection, and hence have historically been exploited as tools for identification of pathogen strain-specific proteins that are produced during an infection; however, the aforementioned limitations of antibodies from hosts following a natural infection for defining panels of proteins that are "shared" among/"conserved" in diverse pathogen variants/strains necessitates adoption of innovative methods to both greatly broaden the antibody repertoire and the magnitude of antibody responses.

In an embodiment the immunization composition includes an adjuvant to further enhance immune response. Any convenient adjuvant may be used, and many are well known to one skilled in the art. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Immunostimulatory agents or adjuvants have been used for many years to improve the host immune responses to, for example, vaccines. Examples, without meant to be limiting, include, *E. coli*, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants may include: (1) lack of toxicity; (2) ability to stimulate a long-lasting immune response; (3) simplicity of manufacture and stability in long-term storage; (4) ability to elicit both cell mediated immunity (CMI) and humoral immune response (HIR) to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present process need not possess all these characteristics. An embodiment provides for administering a strong adjuvant, that is, one that produces a high titer of antibodies. This may be determined, for example, by an assay after immunization, such as a Western blot of ELISA assay or any other convenient method of determining titer of response. In one example, prior experimentation may provide information on a desired high titer response. By way of further example below, a Western blot showing a 1 in 5000 dilution or more or ELISA showing one in 10,000 dilution provides the desired response. This is an example and the precise amounts will vary depending upon the proteins and antibodies involved. In still further preferred embodiments, more than one immunization with the proteome is administered, and two, three or more immunizations may be used to produce the desired level of antibody response.

This forces the host to produce antibodies which target every protein, included those that otherwise are shielded from antibodies by the target organism such as a pathogen. This process in an embodiment is repeated for each variation of the pathogen, where the pathogen is represented by different strains or biotypes. In an embodiment mass spectrometry may be used to analyze the different proteins binding to the antibodies. In a further embodiment, the proteins binding to the resulting antibody library that results from a host immunized with a different biotype may be analyzed by bioinformatics to identify conserved sequences among the different strains. The result is a fast effective means of identifying a conserved region, a unique region, or one which expresses at a different level, which then may be used in any of a variety of processes to provide a therapeutic molecule such as a vaccine to protect an animal from the pathogen.

Here, two methods are shown in which the entire pathogenic/organism proteome is used to generate antibodies that include antibodies against the protein having a sequestered epitope or subject to steric hindrance. Previous methods produce antibodies, if produced at all, which are suboptimal and/or produced in low numbers. By the processes used here, the entire proteome is used to immunize an experimental host animal.

To generate such "enhanced" polyclonal antibodies directed against all proteins and epitopes comprising the pathogen proteome, regardless of their immune potential during natural infection, two innovative methods, Technology for generation of Antibodies against recombinant Pathogen Proteomes (TAPP) and Host Antibody Response Reprinting Technology (HARRT) have been developed. Such "enhanced" antibodies can be adapted to a variety of formats for definition of poorly immunogenic and sequestered shared/conserved proteins and epitopes, respectively.

(1) Technology for generation of Antibodies against Recombinant Pathogen Proteomes (TAPP)

Figure 2:
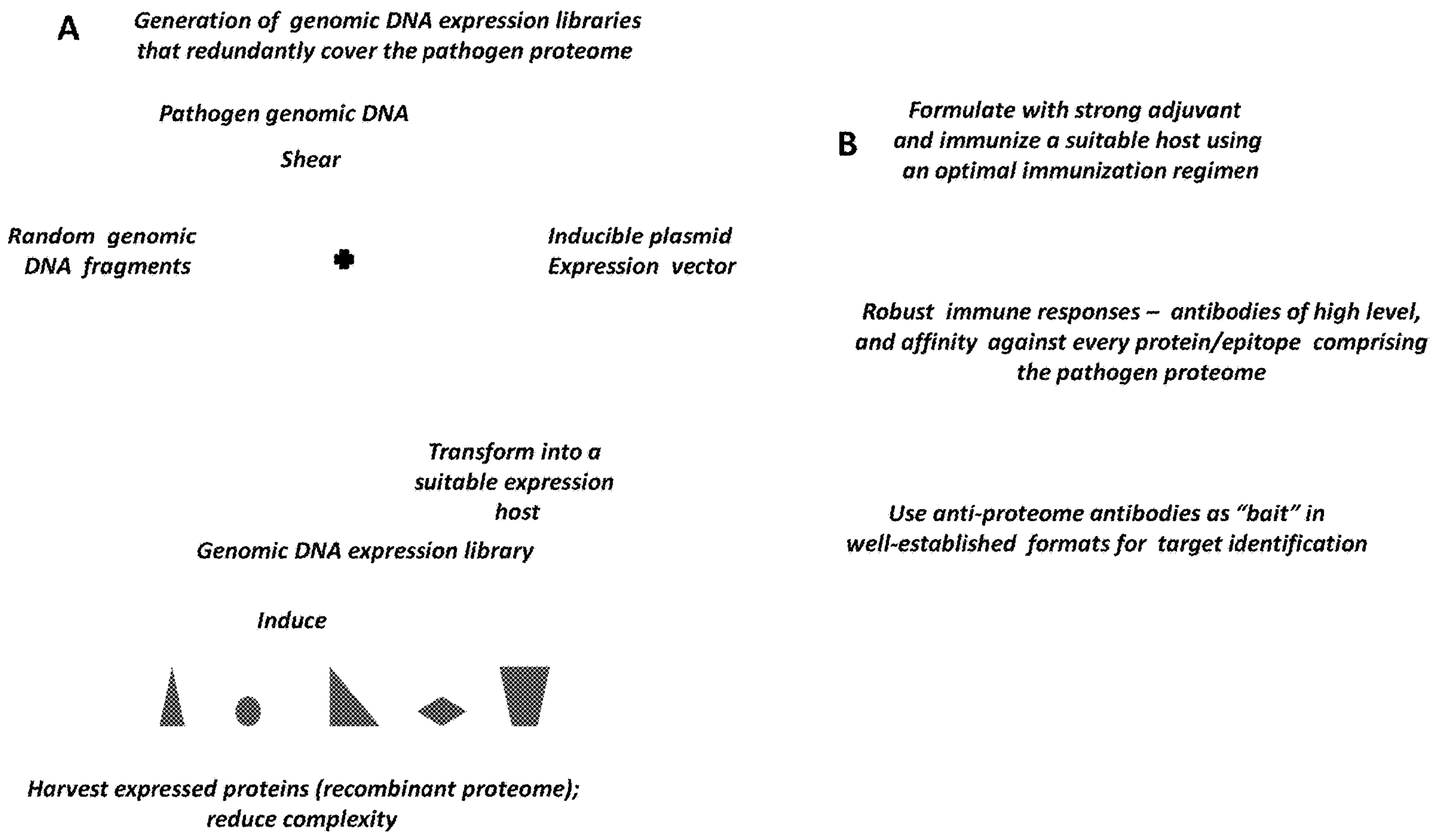
FIG. 2 is a flow chart depicting strategy for generation of anti-proteome antibodies against proteomes encoded by Eglibraries.

The TAPP principle involves construction of inducible, random genomic DNA expression libraries (Eglibraries; FIG. 2) that redundantly cover the proteome of the pathogen of interest, or cDNA expression libraries (FIG. 3; EcDNAlibraries) that are representative of cells/tissues of an organism of interest.

Induction of such expression libraries results in expression of recombinant proteins encoded by genes on inserts on plasmids within clones constituting these libraries. Recombinant proteins (recombinant proteome) are harvested, formulated and in an embodiment formulated with a strong adjuvant, and is used en masse to repeatedly immunize a suitable experimental host, a strategy that results in robust antibody responses against every epitope on proteins comprising the pathogen proteome, irrespective of immunogenic potential of such epitopes/proteins during natural infection. The surprising result in using in TAPP is the deployment of Eglibraries/EcDNAlibraries to generate a recombinant proteome of an organism, including pathogen of interest, and its use en masse as the immunogen (molecule[s] that is capable of eliciting antibody) to generate high quality anti-proteome antibodies in an experimental host. When referring to use "en masse" of the proteome is meant the proteome generated by the Eglibraries/EcDNAlibraries is used as the generator of an anti-proteome.

1a.1. TAPP-Experimental Details: Anti-proteome Antibodies Generated Against Proteomes Encoded by Eglibraries (i) Construction of inducible random genomic DNA expression libraries (Eglibrary) of the pathogen of interest. The pET(30) abc expression vectors and three different *E. coli* expression hosts strains, BL21 [DE3] (Invitrogen), general high-level expression; Origami 2 [DE3] (EMD Biosciences), and C41[DE3] (Lucigen) for optimal expression of disulfide bonded and membrane proteins, respectively) are used to generate optimized expression libraries (Eglibraries). Genomic DNA, isolated from the pathogen of interest is used in the construction of three Elibraries per cognate strain. Recombinant proteins are harvested following induction of Elibraries with IPTG from both lysate and pellet fractions.

One Elibrary using genomic DNA isolated from the pathogen of interest (in an example, insert fragment size ranges from 0.3 kbp-1.0 kbp and 0.5-1.5 kbp) is first constructed in the pET 30 abc expression vectors and *E. coli* BL21 (DE3) expression hosts as described earlier by us (Kudva et al., 2006; world wide web.mcponline.org/content/5/8/1514.full.pdf; see also US20120263724, incorporated herein by reference in its entirety), except that inserts are generated using a hydroshear and end-repaired using the End-it Kit (Epicentre) prior to blunt end cloning into the EcoRV site of the pET vectors. This variation is used because when enzymes are used to randomly fragment the DNA to obtain molecules of specific size, the process is limited by the presence of cleavage sites for that particular enzyme—in other words, if those cleavage sites are absent in a particular genome or spaced too far apart, it would not be possible to obtain fragments of the desired size. On the other hand, random mechanical fragmentation results in sheared DNA fragments, the sizes of which can be controlled by adjusting the settings on the instrument.

Figure 6:
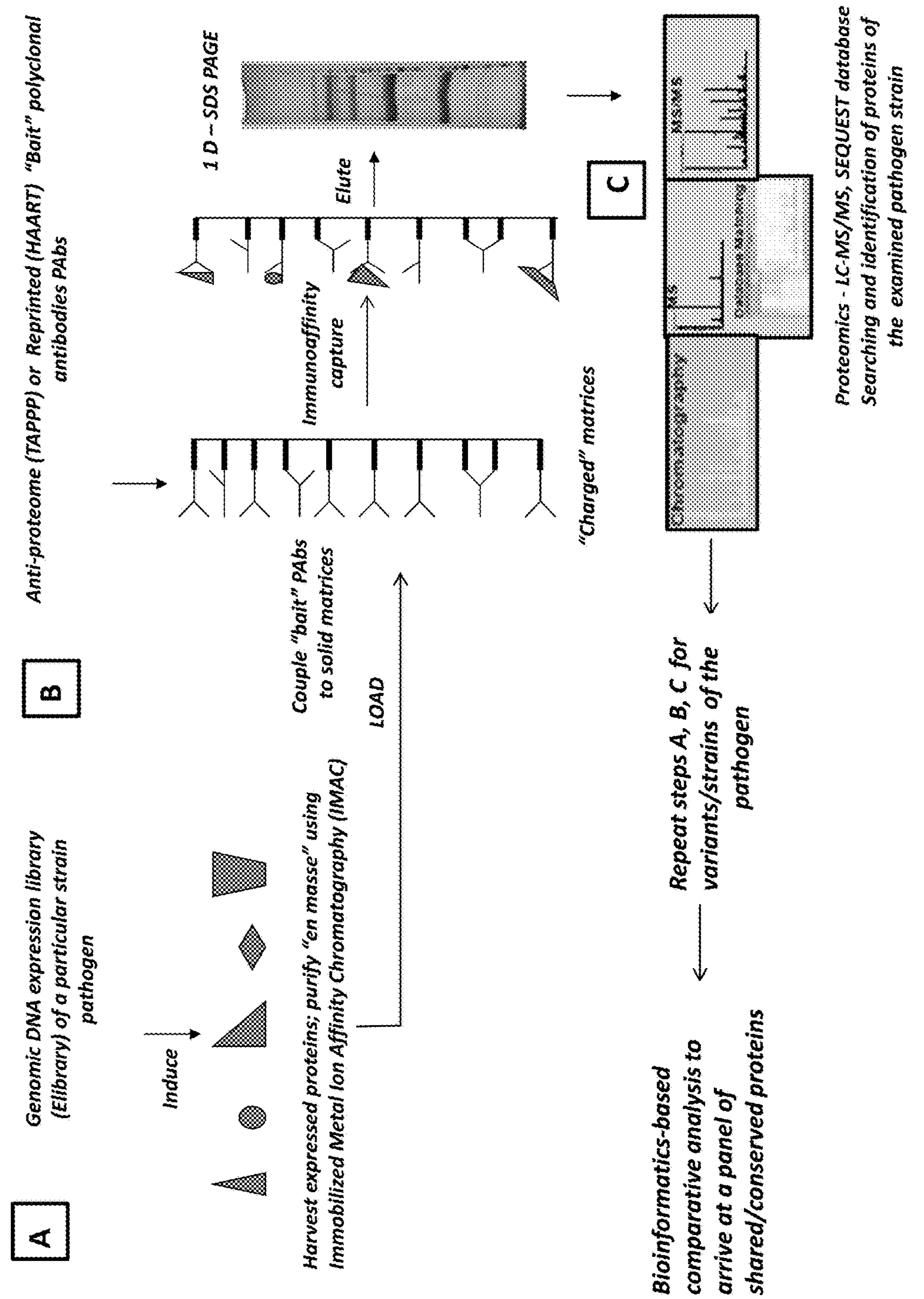
FIG. 6 is a flow chart depicting a model for application of Technology for generation of Antibodies against recombinant Pathogen Proteomes (TAPP) and HAART-derived antibodies for definition of shared/conserved pathogen proteins.

This process known as Proteomics-based Expression Library Screening (PELS). Briefly, proteins from a pathogen are captured from an inducible library of genomic DNA prepared of the sequences pathogen, using polyclonal antibodies specific for the proteins. In one example, such antibodies may be prepared from sera of an infected host or obtained from reservoirs colonized by the cognate pathogen. These are called "bait" polyclonal antibodies and may be coupled to a solid support. Captured proteins are subjected to GeLC-MS/MS; that is liquid chromatography followed by tandem repeat mass spectrometry. Database searching (using such programs as SEQUEST) allows for identification of the proteins within as short a time as three weeks. (See, for example, FIG. 6 and paragraphs 0115-0133 of US20120263724, incorporated herein by reference).

The quality of each Eglibrary may then be determined by confirming the presence of genes encoding previously identified/reported proteins by a convenient method, such as by Southern blotting, where genomic DNA of each strain is probed with purified and labeled amplicons generated using nested primers derived from the above gene sequences. Following confirmation of quality, in an embodiment, each Eglibrary is also transformed into at least two additional libraries which aid in further enhancement of select proteins and redundancy. By way of example, one library which is useful is *E. coli* Origami 2(DE3; which contains mutations in genes encoding thioredoxin reductase and glutathione reductase for optimal expression of disulfide bond containing proteins in the cytoplasm; Novagen). Still another example is the *E. coli* Rosetta-gami B (NOVAGEN) strain, a derivation of Origami that can be used to express mammalian proteins in *E. coli*. A third useful library, by way of example, is *E. coli* C41(DE3:pLysS, which has an uncharacterized mutation(s) that allows for optimal expression of membrane or toxic proteins; Lucigen). The use of the latter two expression host strains, a refinement of the original methodology, provides excellent redundant coverage of the pathogen proteome as evidenced by our current and completed studies with related pathogens. While it is not necessary to use three host strain libraries, here, using multiple libraries had advantages. Each of these hosts strains have a different attribute—for example, Origami cells help proteins with extensive three-dimensional structures that are normally exported from the interior to the outer compartments of the cell to fold correctly in the interior of the cell. Aberrantly folded proteins are destroyed or form insoluble precipitates that can kill the expression host. C41 strains are especially tolerant of toxic and membrane proteins which can kill BL21 hosts. A number of other host strains are available, and the process is not limited to these strains. An embodiment provides more than one host strain library is selected based upon its ability to enhance or prevent inhibition of particular proteins or adverse impact of such proteins. The libraries thus differentially express proteins of the proteome. In an embodiment, multiple host strain libraries are used and in another embodiment, a total of three Eglibraries of a pathogen of interest are constructed.

Eglibraries thus generated are cultured and in one embodiment cultured to an initial $OD_{600}$ of about 0.5 to 0.8 and in another embodiment about 0.6 and induced with 0.5 mM of IPTG, followed by overnight growth at 25° C. The recombinant proteome in lysate and pellet fractions of cells comprising the Eglibraries, following harvest, is then subjected to chromatography, and in an example subjected to Immobilized Metal Ion Affinity Chromatography (IMAC) to purify "en masse" recombinant proteins by exploiting vector-derived affinity handles, such as hexa-histidine tags (SEQ ID NO: 13). IMAC reduces complexity of the recombinant proteome by enriching for proteins of the pathogen of interest and facilitates their fractionation from proteins of the expression bacterial host. The enriched pathogen proteome may then be desalted into 0.1 M Na Phosphate (pH 7.4) buffer and serves as the immunogen.

(ii) Immunization and generation of anti-proteome antibodies in a suitable host. To generate anti-proteome PAbs, the enriched recombinant proteome, comprising recombinant proteins expressed from highly functional Eglibraries are the immunogens as illustrated by the following example. For this, the pathogen proteome purified via IMAC from each of the three Elibraries of the pathogen of interest is pooled, applied to a FPLCMono Q anion exchange column (~50 mg of total protein in 5 ml of 50 mM sodium phosphate buffer, pH 7.2), and eluted using a 15-min high salt (0.5 M NaCl) gradient. Elution fractions and the no-stick fraction are grouped into three pools, concentrated, quantitated using a nomograph alignment chart (Bollag DM, Rozycki, M.D., Edelstein, S.J. eds, 1 *Protein Methods* 2d Edit. Wiley-Liss, New York, 1996), formulated with the adjuvant, Titermax Gold (Sigma), and then used to immunize a suitable experimental host. The success of immunization is assessed by examining the reactivity of the generated anti-proteome antibodies against individual immunogen pools; initially in western blots, with the cognate immunogen pool as the target, followed by confirmation and quantification using an ELISA format. A western blot profile of strong and broad reactivity and an ELISA titer equal to or better than 1:50,000 is construed as evidence of successful immunization, in the absence of which additional boosting is done until these results are achieved. The "enhanced" anti-proteome polyclonal antibodies, generated in this manner, are adsorbed against IMAC-purified proteins encoded by the native pET30(abc) vector-specific DNA sequences prior to use as "bait" antibodies in well-established protocols for target identification.

Experimental Validation of "Technology for Generation of Antibodies Against Recombinant Pathogen Proteomes or TAPP Using Recombinant Expression Genomic DNA or EgDNA Libraries [FIG. 2]

Background.

These studies were funded by a United States Department of Agriculture (USDA) Small Business Innovation Research (SBIR) project that was focused on the development of a highly efficacious universal protein subunit vaccine to protect chickens against infection with the human pathogens, *Campylobacter jejuni* and *Campylobacter coli*. The objective of a study was to define a panel of proteins with vaccine potential conserved across temporally and spatially diverse *C. jejuni* (20 strains) and *C. coli* (10 strains) toward a protein subunit vaccine capable of broadly protecting infection/colonization of gastrointestinal tracts of poultry by different strains of these pathogens. Such a vaccine would significantly reduce the incidence of human disease, since chickens are the principal source of human Campylobacteriosis. The efficacy of the resulting experimental vaccine validates the approach outlined, wherein recombinant proteomes were used to generate "enhanced anti-proteome antibodies," which were then employed in a powerful proteome mining format to identify vaccine candidates that comprised the experimental cross protective vaccine.

Experimental Details.

The experimental procedures are along the lines outlined in section 1a.1 above in the provisional application, and include the following:

(i) Generation of *C. jejuni* strain RM 1221 (RM 1221) anti-proteome PAbs in mice. As outlined in FIG. 2, recombinant proteins from lysate and pellet fractions of three Eglibraries *C. jejuni* strain RM1221 (a sequenced chicken isolate that causes human *Campylobacter* disease) were pooled, formulated with a potent adjuvant and used to generate anti-proteome "enhanced" PAbs in mice for defining a panel of conserved proteins (below). The immunogen mixture comprised of en masse IMAC-purified recombinant proteins from each of the three Elibraries of RM1221, immunologically depleted of *C. jejuni* housekeeping proteins. The immunogen mixture was then further subjected to anionic chromatographic fractionation, and three pools, concentrated, quantitated and formulated with alum were used to immunize five mice/pool. The success of immunization was assessed by examining the reactivity of the generated anti-proteome PAbs against individual immunogen pools; initially in western blots, with the cognate immunogen pool as the target. The generated anti-proteome PAbs were adsorbed against IMAC-purified proteins encoded by the native pET30 (abc) vector-specific DNA sequences prior to use as "bait" PAbs in immunoaffinity capture.

(ii) Construction of "optimized" inducible genomic DNA expression libraries (EgDNA libraries). We utilized the pET(30) abc expression vectors (Novagen) and three different *E. coli* expression hosts strains, BL21 [DE3] (Invitrogen), general high-level expression; Origami 2 [DE3] (EMD Biosciences), and C41[DE3] (Lucigen) for optimal expression of disulfide bonded and membrane proteins, respectively) to generate optimized expression libraries (Elibraries). For this genomic DNA was isolated each of the 30 *Camyplobacter* strains/isolates, and fragments in the range of 0.5-1.5-kbp were cloned into the pET (30) abc expression vectors and then first transformed into *E. coli* DH5 alpha. The quality of this primary Elibrary by confirmed by determining the presence of genes encoding highly conserved proteins, CjaA and CjaD, by probing genomic DNA with the amplicons generated using nested PCR of the cognate Elibrary. Each Eglibrary was then propagated, and plasmids isolated and used to transform *E. coli* BL21 (DE3), the recommended host strain. The isolated plasmids were also used to transform *E. coli* Origami 2 [DE3], and C41[DE3] resulting in generation of secondary Elibraries. To generate recombinant proteins, each Eglibrary was cultured with shaking at 250 rpm at room temperature to an $OD_{600}$ of 0.6 and then induced with 0.5 mM IPTG overnight. Recombinant proteins harvested were from pellet and lysate fractions following 3 cycles of freeze-thaw and 3 cycles of sonication, and stored at −70° C. in PBS-0.2% NOG until further use.

(iii) Definition of a panel of conserved proteins. Anti-proteome PAbs generated against RM 1221 were used as "bait" in Proteomics-based Expression Library Screening (PELS; a published proteomics-based format for protein antigen identification [Kudva IT, Krastins B, Sheng H, Griffin RW, Sarracino D, Tarr PI, Hovde CJ, Calderwood SB, and John M. Proteomics-based Expression Library Screening (PELS). 2006. A Novel Method for Rapidly defining Microbial Immunoproteomes. Molecular and Cellular Proteomics; 5:1514-1519; worldwide web.mcponline.org/content/5/8/1514.full.pdf]), along the lines detailed in FIG. 6 of the application, to sequentially immunoaffinity capture proteins expressed by Elibraries of each of the remaining 29 representative *Campylobacter* strains. Following LC-MS/MS and identification of specifically captured proteins of each strain by querying *Campylobacter* sequences with the output spectral data in non-redundant databases, we used specialized bioinformatics-based algorithms to compile the panel of conserved proteins. In particular, we identified identical/near-identical proteins using the standard alignment software program, KALIGN 2.0 (An example of alignment in ClustalW format is shown elsewhere in this application), We then defined a group of disparate (distantly related) proteins that shared short linear epitopes using the multiple sequence alignment algorithm called T-Coffee PSI (world wide web. Tcoffee.org; Representative examples to demonstrate the functioning of this software and output are shown in FIG. 7A-C and FIG. 8A-C of this application), and followed this up by examining all disparate proteins using a structure-based multiple alignment algorithm called 3D-Coffee/Expresso (world wide web.Tcoffee.org; not shown) for identification of possible discontinuous/assembled epitopes of distantly related proteins.

Results of the Study.

The above experimental approach and subsequent bioinformatics-based analysis resulted in the identification of a panel of 88 high quality immunologically cross reactive proteins (conserved proteins or CPs). Upon further analysis, the identified CPs (i) were encoded by genes that localized all over the genome; (ii) were of diverse functional classes, including transporters, lipoproteins, sensors of signal transduction systems, extracellular matrix binding proteins, putative adhesins, those involved in chemotaxis, iron regulation, invasion, respiration, periplasmic proteases, chaperones, outer membrane proteins, and unknown proteins; and (iii) localized to all cellular compartments as determined bioinformatically.

The identified CPs included those that had been identified previously by other studies and included proteins such as FlaA, FlaC, CadF, PglB, FlpA, Cj0977 proteins, all of which have been reported to be encoded by genes present across diverse *Campylobacter* strains (Gripp E, Hlahla D, Didelot X, Kops F, Maurischat S, Tedin K et al. 2011. Closely related *Campylobacter jejuni* strains from different sources reveal a generalist rather than a specialist lifestyle. *BMC Genomics*. 12:584). Furthermore, these proteins have also been implicated as playing a role in vivo, i.e., in infection of both murine and avian GIT (Croinin TO, and Backert S. 2012. Host epithelial cell invasion by *Campylobacter jejuni*: trigger or zipper mechanism? *Frontiers in Cellular and Infection Microbiology*. 2. 1-13). These facts serve as an internal control and validate both our experimental approach and the findings of our study. Because 82/88 CPs, included a group not yet implicated in infection/colonization of the avian GIT, we evaluated these proteins further and experimentally determined a subset 28 of the 82 proteins to be cell-surface located. We formulated an experimental vaccine comprised of these 28 cell-surface proteins for in vivo studies in a mouse model of *Campylobacter* colonization.

Because the objective is to develop a rational, multi-component protein subunit vaccine that is broadly protective against both *C. jejuni* and *C. coli*, we sought to determine in a pilot study whether an immunogen mixture including all of these 28 proteins from *C. coli* delivered optimally to the murine mucosal immune system could negatively impact infection/colonization of the mouse GIT by *C. jejuni* RM1221. To do this, we first generated an immunogen mixture comprising of recombinant versions of each of the 28 proteins encoded by the genome of *C. coli* RM 2228 that had been purified by metal affinity chromatography. We immunized a "test" cohort (n=4) of 6-7 week-old female BALB/c mice via the intradermal route using 250 μg (per administration) of the immunogen mixture admixed with 5 μg of cholera toxin (50 μl total volume) as a mucosal adjuvant on days 0, 7 and 14. A control cohort was immunized with 5 μg of cholera toxin alone in 50 μl of PBS. Mice were then challenged via the oral route with $10^6$ CFU of *C. jejuni* RM1221 on day 28. Protection from infection for this pilot study was assessed by duration of fecal shedding. Stool pellets were collected every 12 h following challenge, processed and plated on Campy Blood-Free Selective agar plates (containing charcoal and CVA antibiotics; Hardy Diagnostics). Plates were incubated under microaerophilic conditions at 42° C. for 48 h, and scored for the growth of small grayish and flat colonies (characteristic morphology of *Campylobacter* spp. on this medium). Our results showed that 48 h following challenge, 3/4 mice in "test" cohort and cleared infection as evidenced by no CFU upon fecal culture, whereas 3/4 mice in the "control" cohort continued to shed between 10-$10^2$ CFU of the pathogen in feces. We calculated vaccine efficacy 48 h following challenge to be 67% (given by the formula [ARU×ARV/ARU]×100 (Weinberg and Szilagyi, 2010. Vaccine Epidemiology: Efficacy, Effectiveness, and the Translational Research Roadmap. The Journal of Infectious Diseases. 201:1607-1610): ARU, attack rate in unvaccinated; ARV, attack rate in vaccinated (here, colonization=attack). Our results suggested that cross protection can be conferred by such a vaccine and also that the efficacy of vaccine derived from this pilot study can be significantly improved by optimizing components, dose, route of administration, and the formulation. Such studies are currently in progress both in mice and in chickens.

1a.2—TAPP-Experimental Details—Anti-proteome Antibodies Generated Against Proteomes Encoded by EcDNAlibraries (NOTE: the example below pertains to construction of EcDNAlibraries using mRNA from brains of mice, note that EcDNAlibrary construction follows the same principle for pathogens as well).

(i) Construction of an expression cDNA library using mRNA isolated from thalamus/cerebral cortex of brains of healthy mice. For cDNA library construction, mRNA was isolated from thalamus of brains of 10 healthy mice using the Fast Track MAG Maxi mRNA isolation kit (Invitrogen). Following visual confirmation of integrity, mRNAs from each of the ten specimens were pooled and aliquots as the starting material for cDNA synthesis using the Maxima H Minus Double Stranded DNA Synthesis kit (Thermo scientific). To ensure complete coverage of the thalamus proteome, first strand cDNA synthesis was performed using two separate reactions: in one reaction, first strand cDNA was synthesized using Oligo$(dT)_{18}$ primers (SEQ ID NO: 14) as per the instructions of the manufacturer; in the other reaction, random hexamers were employed to prime first strand cDNA synthesis from mRNA templates that lack poly A tails. First strand cDNA synthesis was followed by synthesis of the second strand as per the instructions of the manufacturer. The synthesized double stranded cDNA molecules were then column-purified, size-fractionated, and sectioned into five gel slices that together included the entire spectrum of synthesized cDNA molecules. Following purification of each of the gel slices, cDNA molecules of similar size ranges from each of the two synthesis methods detailed above were pooled, phosphorylated, and cloned blunt-ended into compatible restriction enzyme sites of the T7 cell-free mammalian shuttle expression vector, pT7CFE1-NHis (Thermo scientific), such that cDNA molecules were cloned in translation frame with upstream vector sequences encoding a hexa histidine affinity tag (SEQ ID NO: 13). This process yielded five limited cDNA libraries (one each from cDNA contained in individual gel slices; each limited library upon translation yields a limited proteome). The resulting recombinant limited cDNA libraries were individually propagated in *E. coli* DH5 alpha, and plasmids purified to ultra-purity from each of these libraries for cell-free translation via two sequential column-based purifications followed by a phenol: chloroform extraction and ethanol precipitation. Purity was confirmed both visually and spectrophotometrically.

(ii) Expression of the mouse thalamus cDNA expression library, and IMAC-based purification of expressed proteins. Cell-free translations were performed using the 1-Step Human High Yield Coupled IVT Kit (Thermo scientific) along the lines recommended by the manufacturer with modifications as follows: reactions were set up as instructed by the manufacturer, in 2× the recommended volume containing ultra-pure cDNA preparations at concentrations ranging from 10-100 μg. At 4-hour intervals during incubation, each reaction was replenished twice with one half volume of the reaction mix (without template cDNA), transferred and allowed to proceed in fresh tubes. Following incubation of the reactions for 18 h, translated proteins, which are expressed as fusions with an N-terminal hexa histidine tag (SEQ ID NO: 13), were purified to homogeneity/near homogeneity using IMAC (Hi Trap Metal Ion/Nickel columns; GE Healthcare Life Sciences; IMAC purified proteins) as recommended by the manufacturer, visualized via SDS-PAGE, quantitated and formulated for immunization.

By way of example, this cDNA library was produced with the following process.

Experimental Modifications of the Manufacturers' Recommended Protocol for "En Masse" Expression of a cDNA Expression Library in a Cell-free Translation System The following modifications were incorporated into the manufacturers' recommended protocol in order to ensure expression of every cDNA molecule comprising the library:

(i) Reduction of complexity of the cDNA expression library. The expression library comprises hundreds to thousands of individual cDNA molecules cloned into a plasmid shuttle vector (recombinant cDNA molecules) for translation in the cell-free system. To reduce complexity and better improve the odds of translation of every cDNA molecule, the entire recombinant cDNA library was fractionated on a 1% agarose gel, sliced into five sections to yield 5 limited libraries, and propagated in a laboratory strain of *Escherichia coli*. The recombinant cDNA molecules from each of these five sections constituted a limited cDNA expression library, which was subjected to translation in five different cell-free translation reactions.

(ii) Generation of ultrapure recombinant cDNA molecules that served as templates in the cell-free translation reactions. Following isolation from *E. coli* cultures, recombinant cDNA containing plasmids constituting each limited library was subjected to two disparate but complementary purification strategies to ensure complete removal of contaminants that could potentially interfere with translation. This is a critical modification that directly influences the efficiency of expression a cDNA expression library in a cell-free translation system. One skilled in the art has available many ways of purifying DNA such that undesired materials such as contaminating RNA are reduced or removed. By way of example without limitation, purity of DNA could be analyzed spectrophotometrically at 230, 260 270 and 280 nm. Readings at 230 and 270 should be less than the reading at 260 and the 260/280 ratio of 1.8 is considered satisfactory in an example. Another example provides for inspection visually on an agarose gel to ensure there is no contaminating RNA in the preparation. In an example, without limitation of providing for two complementary but disparate purification strategies is that one first uses a commercially available column-based kit for isolation and purification of plasmid DNA (for e.g., Qiagen plasmid midi or maxi kit), and then follow this up by further purifying the purified plasmids via phenol:chloroform extraction and ethanol precipitation.

(iii) Experimental optimization of concentration of cDNA molecules constituting each limited expression library for use in the cell-free translation system. Optimization of concentration of cDNA was performed, given that the manufacturers' recommended protocol is optimized for expression of only a single/few cDNA molecules in one reaction. Our studies revealed that the range of optimal concentration of each limited cDNA library for effective translation was 10-100 micrograms.

(iv) Experimental determination of optimal reaction conditions for cell-free translation. Because the manufacturers' recommended protocol does not provide experimental details for "en masse" translation of an expression cDNA library, and also to ensure that the cell-free translation of each limited cDNA expression library yielded adequate amounts of proteins for downstream analysis, a series of experiments were performed to arrive at the set of reaction conditions for effective translation of each limited expression cDNA library. Specifically, each cell-free translation reaction was set up and allowed to proceed at the recommended temperature. After 4 hours, one half volume of the reaction was transferred into a new tube containing an equal volume of fresh reaction components and allowed to proceed for another 4 hour. This process was then continued every 8 hours for a total duration of 24 hours. Such modifications allowed for expression of all proteins, including those that are difficult-to-express in adequate amounts. Although currently unclear, dilution of template recombinant cDNA molecules resulting in less interference from proteins that are efficiently translated, replenishment of raw materials for translation, and further reduction of complexity of each limited cDNA library had probable roles to play. Protein expression was followed by SDS-PAGE and Coomassie blue staining.

(iii) Generation of anti-proteome polyclonal antibodies in chickens. IMAC-purified proteins constituting each limited proteome were pooled, and immunologically depleted of contaminants via sequential adsorptions using antibodies (covalently linked to Dynabeads M-280 Tosylactivated [Life Technologies]) previously generated against HeLa whole cells and cell lysates, which are the source of the translational machinery in the kit. The enriched recombinant proteome was concentrated, quantitated using a nomograph, formulated with the adjuvant, Titermax Gold (Sigma), and then used to immunize phylogenetically distinct hosts, namely chickens. Approximately 750 μg of total protein plus adjuvant (per dose) was used to immunize two chickens as one primary and two booster immunizations. The success of immunization was assessed by examining the reactivity of the generated anti-proteome antibodies against the immunogen using an ELISA format, which indicated a titer equal to or better than 1:5,000. The functionality of the generated anti-proteome polyclonal antibodies was demonstrated in an experimental study to determine proteins either conserved/unique to or expressed at significantly higher levels in thalamus/cortex of brains of mice subjected to blast-mediated TBI. This was done by depleting a recombinant proteome of the thalamus/cortex of brains of mice with blast-induced TBI using the anti-proteome antibodies generated in chickens against the recombinant proteomes of thalamus/cortex of brains of healthy mice (i.e., by generating a depletome [TBI-depletome; depletome is defined as the complement of residual molecules in a complex mixture following subtraction of confounding molecules]), followed by proteomics-based analysis of the TBI-depletome and immunohistochemistry-based validation of one of the proteins comprising the TBI-depletome (described below in the following section).

(iv) Demonstration of an application of the generated chicken anti-proteome antibodies—TBI-depletome analysis for definition of proteins either conserved/unique to or differentially expressed in the thalamus/cortex of brain of mice with TBI. An expression cDNA library was constructed using mRNA isolated from pooled thalamus/cortex of brains of 10 mice 28 days following experimental blast-mediated TBI as described above, and expressed using the cell-free in vitro translation system exactly as described in the previous section. Following IMAC purification, an enriched TBI proteome was obtained following immunological subtraction using anti-HeLa polyclonal antibodies generated by us in an earlier study as described in the previous section. The enriched TBI proteome was then subjected to a series of adsorptions using the chicken anti-proteome antibodies (generated as detailed in the previous section) covalently linked to Dynabeads M-280 Tosyl activated. Adsorptions were performed until there was a complete lack of reactivity of the chicken anti-proteome antibodies with the components of the TBI-depletome as determined by western blotting. The resulting TBI depletome, depleted of proteins specific to thalamus/cortex of brains of healthy mice, but enriched for those conserved or uniquely present or expressed at significantly higher levels in thalamus/cortex of brains of TBI-induced mice was subjected to one dimensional SDS-PAGE and tandem mass spectrometry (GeLC-MS/MS) for protein identification.

Proteomics-based analysis resulted in the identification of 25 proteins that were either conserved/unique to or differentially expressed in the thalamus/cortex of brains of mice with TBI. Identified proteins were correlated bioinformatically with both molecular pathways triggered and specific expression in the thalamus. The identified pathways and the number of players involved in each pathway are shown in Table 1.

TABLE 1

Pathways activated 28 days following TBI

| Pathway | Number of proteins identified in each pathway |
|---|---|
| Neurodegeneration and mitochondrial stress | 14 |
| Axon guidance | 5 |
| Neurotrophin signaling | 3 |
| Gap junctions | 3 |

Figure 4:
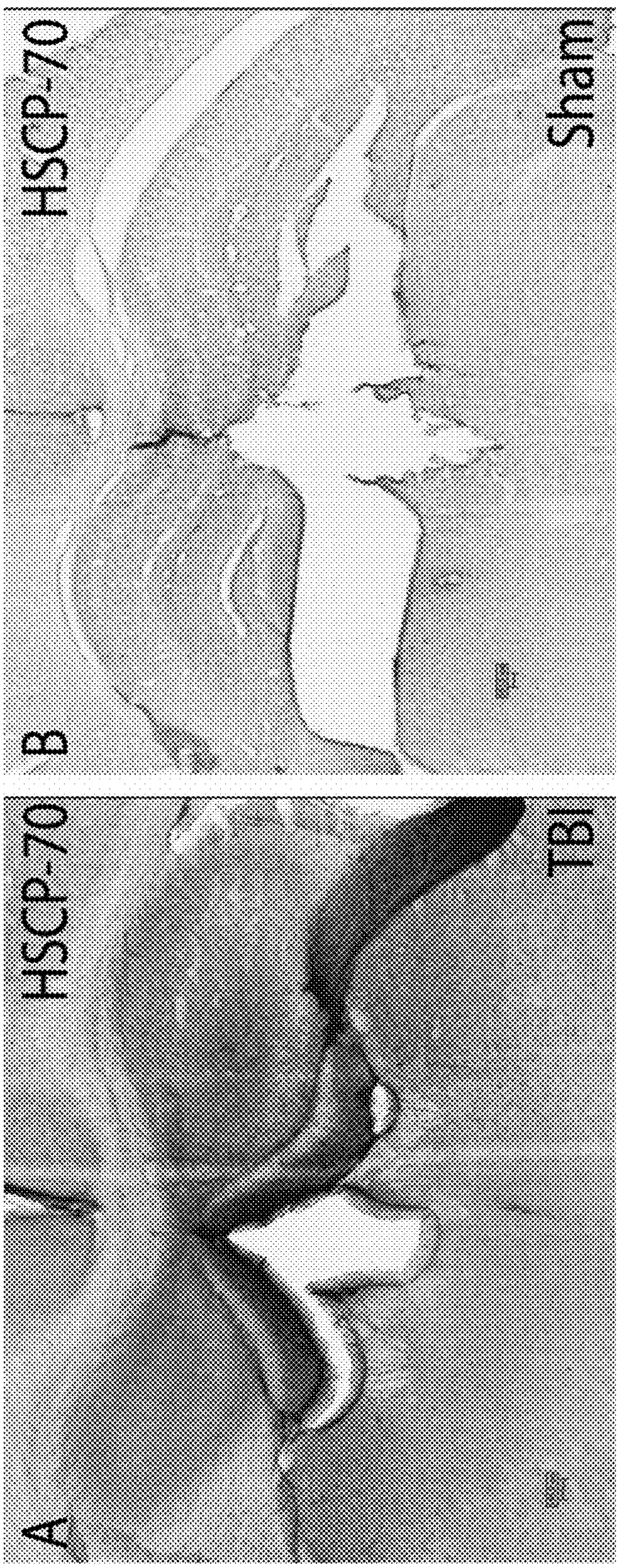
FIG. 4 is a photo demonstrating differential expression of HSCP-70, a component of the TBI-depletome identified using chicken anti-proteome antibodies generated against the proteome encoded by an expression library constructed using cDNA (EcDNA library) isolated from thalamus/cortex of brains of healthy mice.

The differential expression of one such protein was studied via immunohistochemistry. In particular, Heat-shock cognate protein-70 (HSCP-70) was demonstrated to be highly expressed in the brains of mice after blast-mediated TBI (and hence conserved or unique to thalamus/cortex of brains of mice with TBI) (see dark staining of FIG. 4A), where sham-blast mice did not show an upregulation of HSCP-70 (FIG. 4B). Scale bar in each image is 100 μm. Interestingly, the function of HSCP-70 is involved with synaptic plasticity and aberrant tau accumulation, which has been shown to be the major pathology of blast-mediated TBI (Alisambra et al., 2013; worldwide web ncbi.nlm.nih.gov/pmc/articles/PMC3733249/pdf/nihms486201.pdf).

Also alluding to the relevance of the identified proteins of the TBI-depletome was that fact that ~50% of such proteins were immunogenic in the host, i.e., elicited antibody responses in mice with TBI (data not shown), suggesting Biomarker potential. Interestingly, a subset (~35%) of the immunogenic proteins has also been reported as putative Biomarkers of TBI in humans, which is a further attestation of the functionality of the generated chicken anti-proteome antibodies. Studies are underway to investigate Biomarker potential of the remaining proteins comprising the TBI-depletome.

(2) Host Antibody Response Reprinting Technology (HARRT)

Figure 5:
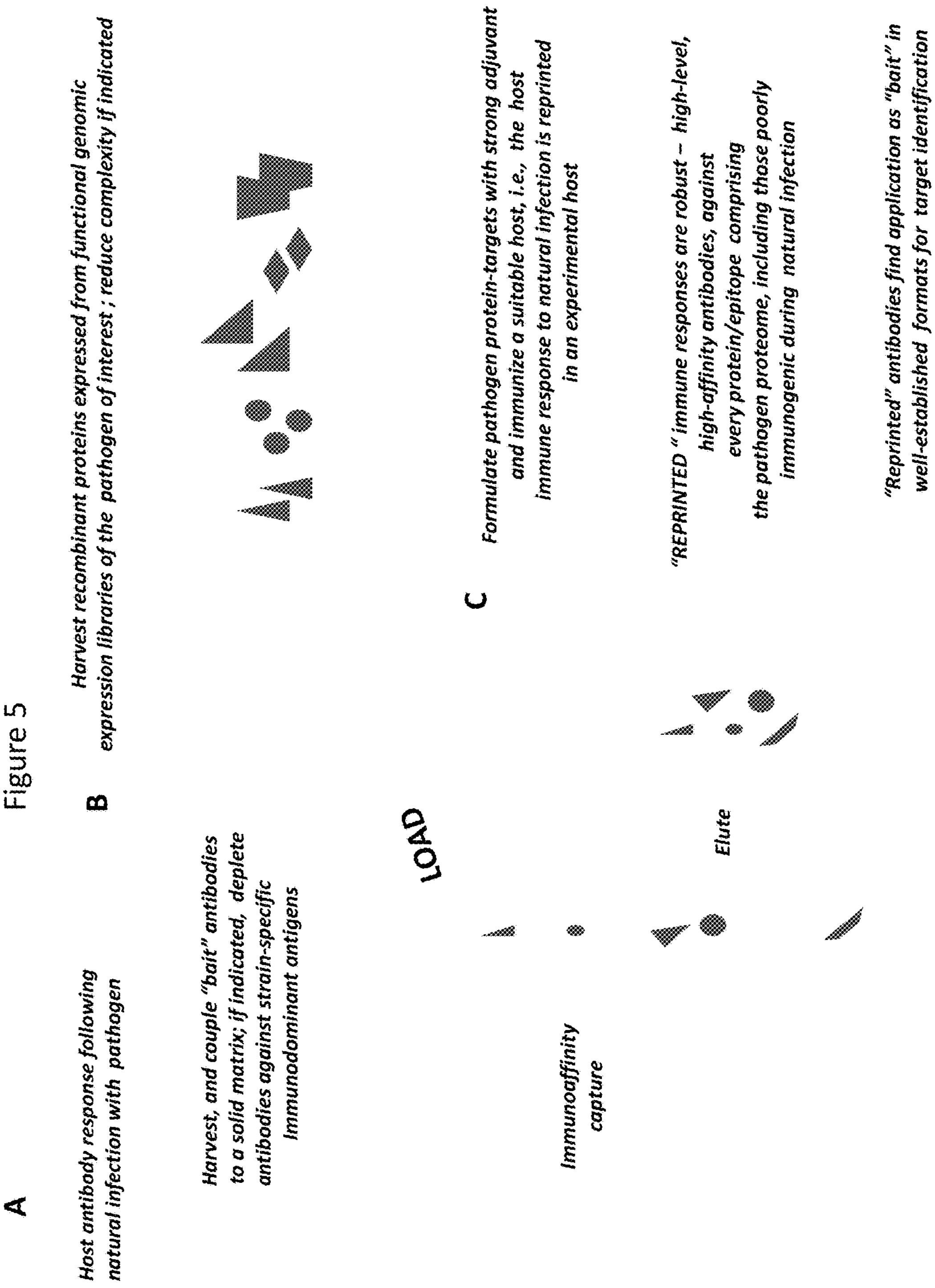
FIG. 5 is a flow chart depicting Host Antibody Response Reprinting Technology (HAART).

HARRT is a novel strategy for generating robust immune responses that include high-level and high affinity polyclonal antibody responses that are equally focused on pathogen proteins that are poorly immunogenic (ability of a molecule to elicit an immune response) during natural infection/disease. The HARRT principle (FIG. 5) involves the experimental "reprinting" of the antibody response mounted by a host in response to a natural infection infection/disease.

The HARRT procedure exploits the affinity of polyclonal antibodies produced by the host to proteins that are expressed by a pathogen during natural infection/disease. Hence, HAART involves immuno-affinity capture of recombinant proteins expressed from genomic Elibraries of a pathogen of interest by covalently immobilized polyclonal "bait" antibodies. Specifically captured recombinant protein targets are eluted and in a preferred embodiment are formulated with a strong adjuvant, and then used to optimally immunize an appropriate experimental host.

This strategy wherein the host immune response during natural infection is reproduced in an experimental host is referred to as "reprinting." When optionally combined with strong adjuvants and optimal immunization regimens, "reprinting" allows generation of robust levels of high affinity antibodies that are directed against all constituents of the pathogen immunoproteome, including those proteins/epitopes that engender only suboptimal (low-level) antibody responses during natural infection, owing to their poor immunogenic potential. This new process changes the manner in which host immune responses are redirected toward and focused on the complement of pathogen proteins that are not the primary targets during natural infection. The term "reprinting" is used since the host antibody response is still directed against all IVE proteins (i.e., resembles the original host immune response), but now is focused equally on those that are sub-immunodominant during natural infection as well. A variation of this technology is the ability to focus the "reprinted" antibody response uniquely (by depleting immunodominant pathogen proteins from the immunogen mixture) on pathogen proteins that remain sub-immunodominant during natural infection, if indicated.

HARRT (FIG. 5)—Experimental Details

Purification of Antibodies from Body Fluids of Hosts Following Natural Infection/Disease.

Polyclonal antibodies from body fluids of hosts are affinity purified using any convenient method. Many methods are available to one skilled in the art to purify antibodies and any convenient method may be used. By way of example, without limitation, is to immobilize the proteome on a solid matrix and then purify antibodies from host body fluids. Protein L is another matrix that can be used to purify antibodies by a procedure similar to that used for Protein A/G. In an example, either or both Protein A/Protein G coupled matrices, including magnetic Dynabeads, may be used as instructed by the manufacturer. This is because Protein A reportedly binds all human immunoglobulin (Ig) isotypes and IgG subclasses except IgG3, whereas protein G binds all IgG subclasses but not other Ig isotypes. Specifically, for capture of antibodies by Dynabeads protein A, 10 μl of pooled immune sera is to 100 μl of beads, prepared according to the manufacturer's instructions, and incubated at room temperature with slow tilt rotation for 30 min. The beads are then pulled down using a magnet, the supernatant decanted, and beads washed according to the manufacturer's instructions to remove loosely bound components. Specifically bound Igs are then eluted with 0.1 M citrate (pH 3.0) directly into 1 M Tris (pH 9.0). Affinity purified sera are then stored at 4° C. following the addition of 0.02% sodium azide until further use. Long-term storage is in 50% glycerol at −70° C.

Generation of Functional Eglibraries or EcDNAlibraries Using Genomic DNA or cDNA, Respectively from the Cells/Tissues of an Organism, Including the Pathogen of Interest.

The libraries may be generated using any convenient methods, as is described supra for TAPP.

In one example, when genomic DNA is used, the pET(30) abc expression vectors and three different *E. coli* expression hosts strains, BL21 [DE3] (Invitrogen), general high-level expression; Origami 2 [DE3] (EMD Biosciences), and C41 [DE3] (Lucigen) for optimal expression of disulfide bonded and membrane proteins, respectively) are used to generate optimized expression libraries (Elibraries). Genomic DNA, isolated from the pathogen of interest is used in the construction of three Elibraries per cognate strain. Recombinant proteins are harvested following induction of Eglibraries with IPTG from both lysate and pellet fractions.

One Eglibrary using genomic DNA isolated from the pathogen of interest (in an example, insert fragment size ranges from (0.3 kbp-1.0 kbp and 0.5-1.5 kbp) is first constructed in the pET 30 abc expression vectors and *E. coli* BL21 (DE3) expression hosts as described earlier by us (Kudva et al., 2006; worldwide web.mcponline.org/content/5/8/1514.full.pdf), except that inserts are generated using a hydroshear and end-repaired using the End-it Kit (Epicentre) prior to blunt end cloning into the EcoRV site of the pET vectors. The quality of each Eglibrary is then determined by confirming the presence of genes encoding previously identified/reported proteins by Southern blotting, where genomic DNA of each strain is probed with purified and labeled amplicons generated using nested primers derived from the above gene sequences. Following confirmation of quality, each Eglibrary is also transformed into *E. coli* Origami 2(DE3; which contains mutations in genes encoding thioredoxin reductase and glutathione reductase for optimal expression of disulfide bond containing proteins in the cytoplasm; Novagen) and *E. coli* C41(DE3:pLysS, which has an uncharacterized mutation(s) that allows for optimal expression of membrane or toxic proteins; Lucigen). The use of the latter two expression host strains, a refinement of the original methodology, provides excellent redundant coverage of the pathogen proteome as evidenced by our current and completed studies with related pathogens. Hence, a total of three Eglibraries of a pathogen of interest are constructed. Eglibraries thus generated are cultured and in one embodiment to an initial OD600 of 0.6 and induced with 0.5 mM of IPTG, followed by overnight growth at 25° C. The recombinant proteome in lysate and pellet fractions of cells comprising the Eglibraries, following harvest, is then subjected to Immobilized Metal Ion Affinity Chromatography (IMAC) to purify "en masse" recombinant proteins by exploiting vector-derived affinity handles, namely hexahistidine tags (SEQ ID NO: 13). IMAC reduces complexity of the recombinant proteome by enriching for proteins of the pathogen of interest and facilitates their fractionation from proteins of the expression bacterial host.

In another example, for organisms and pathogens other than bacteria, the construction of an expression cDNA library (EcDNAlibrary) is as described above under 1a.2 supra. Specifically, mRNA is performed using the Fast Track MAG Maxi mRNA isolation kit (Invitrogen), as per the manufacturer's instructions. Following visual confirmation of integrity, mRNAs are used as starting material for cDNA synthesis using the Maxima H Minus Double Stranded DNA Synthesis kit (Thermo scientific). To ensure complete coverage of the proteome, first strand cDNA synthesis is performed using random hexamers (if bacterial mRNA) or using Oligo$(dT)_{18}$ primers (SEQ ID NO: 14) or random hexamers (if higher organism) as per the instructions of the manufacturer. First strand cDNA synthesis is followed by synthesis of the second strand as per the instructions of the manufacturer. The synthesized double stranded cDNA molecules are then column-purified, size-fractionated, and sectioned into five gel slices that together include the entire spectrum of synthesized cDNA molecules. Following extraction and purification of cDNA molecules from each of the gel slices, cDNA molecules of similar size ranges from each of the two synthesis methods detailed above were pooled, phosphorylated, and cloned blunt-ended into compatible restriction enzyme sites of the T7 cell-free mammalian shuttle expression vector, pT7CFE1-NHis (Thermo scientific), such that cDNA molecules are cloned in translation frame with upstream vector sequences encoding a hexa histidine affinity tag (SEQ ID NO: 13). This process yields five limited cDNA libraries (one each from cDNA contained in individual gel slices; each limited library upon translation yields a limited proteome). The resulting recombinant limited cDNA libraries are individually propagated in *E. coli* DH5 alpha, and plasmids purified to ultra-purity from each of these libraries for cell-free translation via two sequential column-based purifications followed by a phenol: chloroform extraction and ethanol precipitation. Purity of is confirmed both visually and spectrophotometrically.

The proteomes encoded by the limited cDNA libraries generated in the previous step are expressed using appropriate commercially available cell-free translation systems along the lines described in the section 1a.2 supra. Following expression, proteins constituting each limited proteome, which are expressed as fusions to a hexa histidine affinity tag (SEQ ID NO: 13) at their amino termini, are purified to homogeneity/near homogeneity using IMAC (Hi Trap Metal Ion/Nickel columns; GE Healthcare Life Sciences; IMAC purified proteins) as recommended by the manufacturer, visualized via SDS-PAGE, quantitated prior to immunoaffinity capture (performed with individual limited proteomes).

(i) Immunoaffinity capture of the IMAC-purified recombinant proteome by host polyclonal antibodies produced in response to natural infection/disease. Polyclonal antibodies from sera of hosts following a natural Infection/disease with the pathogen of interest are affinity purified and in one example using either or both Protein A/Protein G as per the instructions of the manufacturer, covalently coupled to Hi-Trap NHS-activated columns ("charged" columns), and then used to effect immunoaffinity capture of the protein targets in the IMAC-purified recombinant proteome encoded by Eglibraries or EcDNAlibraries, as described previously (world wide web.mcponline.org/content/5/8/1514.full.pdf).

(ii) "Reprinting" of the Host Antibody Response to natural infection/disease by a pathogen in an experimental host. Specifically captured proteins from the above steps may be desalted into 0.1 M Sodium Phosphate buffer (pH 7.4), formulated with the adjuvant, Titermax Gold (Sigma), and then used to immunize a suitable experimental host ("Reprinting" of the host antibody response to natural infection). The success of immunization is assessed. In an example, such success by be determined by examining the reactivity of the generated anti-proteome antibodies against the immunogen; initially in western blots, with the cognate immunogen as the target, followed by confirmation and quantification using an ELISA format. A western blot profile of strong and broad reactivity and an ELISA titer equal to or better than 1:5,000 is construed as evidence of successful immunization, in the absence of which additional boosting is done until these results are achieved. The "reprinted" polyclonal antibodies, generated in this manner, are adsorbed against IMAC-purified proteins encoded by the native pET30(abc) vector-specific DNA sequences (for EgDNA libraries) or against the reaction mixture (without the cDNA molecules) comprising the cell-free system used for expression prior to use as "bait" antibodies in well-established protocols for target identification.

In general, the "bait" antibodies are coupled to columns for binding of proteins. By way of example, see paragraph 0121-0122 of US 20120263724 where bait antibodies were coupled to HiTrap NHS-activated HP columns to capture proteins. The captured proteins may then be analyzed, compared to sequences in various databases of interest. Further, proteins of different biotypes may be analyzed to identify nucleic acid/protein molecules that share homology or otherwise reflect a consensus sequence among the biotypes or a sequence unique among the biotypes or proteins which express at different levels in one biotype versus another. When referring to a consensus sequence is not meant the sequence must be identical to each other, but share a degree of similarity that one skilled in the art can identify the region as representative of an immunogenic molecule that provides or expresses an immunogenic response to varying biotypes and is a candidate as a universal antigenic molecule across strains.

When referring to such an immunogenic molecule it is not intended it consist of a specific number of sequences, but rather sequences of the pathogenic organism that provide an immune response when administered to an animal and in an embodiment, to different biotypes.

Analysis of Sequences

Bioinformatics-based comparative analysis will be deployed to examine the individual panels of proteins identified for each variant/strain (biotype) of the pathogen of interest to arrive at a panel of proteins that are shared among/conserved in all of the variants/strains. See FIG. 6. This will done as follows: The identified proteins of each strain (identified by querying completed genomic sequences contained in non-redundant databases using the mass spectral data using the SEQUEST search engine that is part of the proteomics software package) will result in two groups: one comprising of proteins that are identical or homologous in all of the variants/strains examined. The identification of such shared/conserved proteins will be straight forward using standard sequence alignment software, such KALIGN in Clustal W format at http://expasy.org/tools/ or at worldwide web.ebi.ac.uk/Tools/msa/kalign/ (by aligning amino acid sequences of the identified proteins).

Examples of Sequence Comparison of Identical/Homologous Proteins Using KALIGN (i) The amino acid sequences of the nontoxic, receptor binding moiety of the heat-labile enterotoxin (LTB) from two related enterotoxigenic *Escherichia coli* strains (ETEC) is aligned; Amino acid sequence of LTB (103 aa without signal sequence): apqsitelc seyrntqiyt indkilsyte smagkremviitfksgatfq vevpgsqhid sqkkaiermk dtlritylte tkidklcvwn nktpnsiaaismen (SEQ ID NO: 1)

Kalign (2.0) Alignment in ClustalW Format

```
Sequence1
                                        (SEQ ID NO: 2)
apqsitelcseyrntqiytindkilsytesmagkremviitfksgatfq
vevpgsqhidsg

Sequence2
                                        (SEQ ID NO: 2)
apqsitelcseyrntqiytindkilsytesmagkremviitfksgatfq
vevpgsqhidsg

Sequence1
                                        (SEQ ID NO: 3)
kkaiermkdtlrityltetkidklcvwnnktpnsiaaismen

Sequence2
                                        (SEQ ID NO: 3)
kkaiermkdtlrityltetkidklcvwnnktpnsiaaismen
```

(ii) The amino acid sequences of the toxic enzymatic moiety of the heat labile enterotoxin (LTA) from two related ETEC strains are aligned using KALIGN Amino acid sequence of LTA (240 aa without signal sequence): ngdklyradsrp pdeikrsggl mprghneyfd rgtqmninly dhargtqtgf vryddgyvst slslrsahla gqsilsgyst yyiyviatap nmfnvndvlg vysphpyeqe vsalggipys qiyg-wyrvnf gviderlhrn reyrdryyrn lniapaedgy rlagfppdhq awreepwihh apqgcgnssr titgdtcnee tqnlstiylr kyqskvkrqi fsdyqsevdi ynrirnel (SEQ ID NO: 4)

Kalign (2.0) Alignment in ClustalW Format

```
Sequence1
                                        (SEQ ID NO: 5)
ngdklyradsrppdeikrsgglmprghneyfdrgtqmninlydhargtq
tgfvryddgyv

Sequence2
                                        (SEQ ID NO: 5)
ngdklyradsrppdeikrsgglmprghneyfdrgtqmninlydhargtq
tgfvryddgyv

Sequence1
                                        (SEQ ID NO: 6)
stslslrsahlaggsilsgystyylyviatapnmfnvndvlgvysphpye
qevsalggip

Sequence2
                                        (SEQ ID NO: 6)
stslslrsahlaggsilsgystyylyviatapnmfnvndvlgvysphpye
qevsalggip

Sequence1
                                        (SEQ ID NO: 7)
ysqiygwyrvnfgviderlhrnreyrdryyrnlniapaedgyrlagfppd
hqawreepwi

Sequence2
                                        (SEQ ID NO: 7)
ysqiygwyrvnfgviderlhrnreyrdryyrnlniapaedgyrlagfppd
hqawreepwi

Sequence1
                                        (SEQ ID NO: 8)
hhapqgcgnssrtitgdtcneetqnlstiylrkyqskykrqifsdysevd
iynrirnel

Sequence2
                                        (SEQ ID NO: 8)
hhapqgcgnssrtitgdtcneetqnlstiylrkyqskykrqifsdysevd
iynrirnel
```

The other group of identified proteins will be constituted by disparate proteins that either share only linear or/and assembled/discontinuous cross-reactive epitopes with each other. Disparate proteins with shared linear epitopes will be identified using a multiple sequence alignment algorithm called M-Coffee (world wide web.mcoffee.org; worldwide web.tcoffee.org). T-Coffee is a multiple sequence alignment package combining different alignment methods into one alignment. Protein, DNA and RNA sequences can be combined. T-Coffee is a multiple sequence alignment package that is part of the T-Coffee distribution. Rather than computing multiple sequence alignment along, it uses other packages to compute the alignments and T-Coffee combines these into a final alignment. See. E.g., Notredame et al. "T-Coffee: A novel method of multiple sequence alignments" *JMB*, 302(205-217) 2000. A variation called PSI-Coffee is one variation that is very useful for alignment of distantly related sequences (FIGS. 7 and 8). As can be seen in FIGS. 7 and 8, the results are color coded. Red regions are in agreement across all methods, blue regions have poor agreement and are to be discarded, and yellow regions are to be interpreted with caution. Both disparate proteins with and without evidence of linear epitopes are also analyzed using a structure-based multiple alignment algorithm called 3D-Coffee/Expresso, also a part of T-Coffee where original sequences are replaced by homologous structures, templates aligned using structural aligners to provide a structure based multiple sequence alignment (worldwide web.tcoffee.org), for identification of discontinuous/assembled epitopes (not shown).

Example 1

PSI-coffee (aligns distantly related proteins using homology extension) was used to compare two immunologically cross reactive proteins, namely, LTB (124 amino acids; SEQ ID NO: 9) and a Conserved Hypothetical Protein (Conserved; 1275 amino acids; SEQ ID NO: 10) encoded by the genome of the human pathogen, enterotoxigenic *Escherichia coli* (ETEC) H10407. The conserved hypothetical protein was identified using polyclonal antibodies generated against the LTB protein using TAPP (FIG. 2).

PSI-Coffee Alignment Result

The program clearly highlights regions of importance or consistency (denoted by color: red, strongly consistent; yellow, average consistency to be interpreted with caution; blue/purple, poor consistency or not consistent) shared by the two immunologically cross reactive proteins (FIG. 7A-C).

Example 2

PSI-Coffee Alignment Result

The same proteins of example 1 above were used; however, LTB is chimeric and includes a 25 amino acid fragment of CHP (LTB-CHP) (SEQ ID NO: 11) generated for use in vaccine studies.

Thus this alignment compares an ETEC CHP 1275 amino acid sequence (SEQ ID NO: 10) with ETEC LTB-CHP chimeric protein (149 aa) (SEQ ID NO: 12).

What is claimed is:

1. A method for identifying epitopes comprising one or more amino acid molecules of at least two proteomes of an organism that are conserved or unique, the method comprising, a) generating at least one first cDNA expression library of a first recombinant proteome of a first organism by preparing fragments of the genome of said first organism of 0.3 to 1.5 kbp, size-fractionating said fragments into up to five fractions, and cloning said fragments into vectors;

b) generating at least one second cDNA expression library of at least one second recombinant proteome that is a different biotype from said first organism or is a different organism from said first organism by preparing fragments of the genome of said first organism of 0.3 to 1.5 kbp, size-fractionating said fragments into up to five fractions, and cloning said fragments into vectors;

c) expressing said at least one first expression library and said at least one second expression library en masse in a host to produce said first and said at least one second recombinant proteome;

d) harvesting said first and said at least one second recombinant proteome expressed by said first and said at least one second libraries;

e) generating enhanced anti-proteome antibodies which selectively bind to the proteins of said first recombinant proteome; and f) binding said at least one second recombinant proteome to said anti-proteome antibodies to identify amino acid molecules comprising epitopes by (i) detecting any of said amino acid molecules conserved between said first and said at least one second recombinant proteomes, or (ii) detecting any of said amino acid molecules unique to at least one of said recombinant proteomes to identify said amino acid molecules.

2. The method of claim 1, further comprising identifying a nucleic acid molecule that expresses said amino acid molecules.

3. The method of claim 1, wherein said first and second library is a genomic library.

4. The method of claim 1, wherein said target organism is a pathogenic organism.

5. The method of claim 1, wherein said first or at least one second recombinant proteome or both are expressed by said first library or said at least one second library or both in one to five in vitro reactions.

6. The method of claim 1, wherein said anti-recombinant proteome antibodies are produced by administering said first recombinant proteome and at least one adjuvant to a host and producing antibodies.

7. The method of claim 1, further comprising producing at least three recombinant proteomes from at least three different biotypes or tissue or organisms.

8. The method of claim 1, wherein said amino acid molecule comprises at least one epitope.

9. The method of claim 1, wherein said at least one first genomic library is transformed into three hosts, by transforming said at least one first library into a first *Escherichia coli* (*E. coli*) host, a second *E. coli* host and a third *E. coli* host, where each host differentially expresses proteins of said recombinant proteome.

10. The method of claim 1, wherein a conserved molecule is identified.

11. The method of claim 1, wherein said first organism and at least one second organism are different biotypes and identifying an amino acid molecule conserved between said biotypes or unique to at least one of said biotypes.

12. The method of claim 1, wherein said amino acid molecules which do not bind to said anti-proteome antibodies are separated or removed to produce a depletome.

13. The method of claim 1, further comprising identifying at least one of said amino acid molecules or a nucleic acid that expresses a sequence comprising said amino acid molecule as a therapeutic molecule.

14. A method for producing a molecule for use as a therapeutic molecule, the method comprising, a) generating at least one first cDNA library of a first recombinant proteome of a first organism by preparing fragments of the genome of said first organism of 0.3 to 1.5 kbp, size-fractionating said fragments into up to five fractions, and cloning said fragments into vectors;

b) generating at least one second cDNA library of at least one second recombinant proteome that is a different biotype of said first organism or is a different organism from said first organism by preparing fragments of the genome of said first organism of 0.3 to 1.5 kbp, size-fractionating said fragments into up to five fractions, and cloning said fragments into vectors;

c) expressing said at least one first expression library and said at least one second expression library en masse in a host to produce said first and said at least one second recombinant proteome;

d) harvesting said first and said at least one second recombinant proteome expressed by said first and said at least one second libraries;

e) generating enhanced anti-proteome antibodies which selectively bind to the proteins of said first recombinant proteome;

f) contacting said at least one second recombinant proteome with said anti-proteome antibodies to allow binding of said proteins to said antibodies and identifying amino acid molecules by (i) detecting any of said amino acid molecules conserved between said first and said at least one second recombinant proteomes, or (ii) detecting any of said amino acid molecules unique to at least one of said recombinant proteomes to identify said amino acid molecule; and g) using at least one of said amino acid molecules or a nucleic acid that expresses a sequence comprising said amino acid molecule as a therapeutic molecule.

15. The method of claim 1, comprising preparing DNA fragments of said genome of said first or second organism, or both of at least 1 kbp.

16. The method of claim 1, comprising preparing DNA fragments of said genome of said first or second organism, or both of at least 1.5 kbp.

17. The method of claim 1, wherein said fragments are size-fractionated into five fractions.

18. The method of claim 1, wherein said at least one second genomic library is transformed into three hosts, by transforming said at least one second library into a first *Escherichia coli* (*E. coli*) host, a second *E. coli* host and a third *E. coli* host, where each host differentially expresses proteins of said recombinant proteome.

19. The method of claim 9, wherein said at least one second genomic library is transformed into three hosts, by transforming said at least one second library into a first *Escherichia coli* (*E. coli*) host, a second *E. coli* host and a third *E. coli* host, where each host differentially expresses proteins of said recombinant proteome.

* * * * *

SEQUENCE LISTING

```
<160> NUMBER OF SEQ ID NOS: 14

<210> SEQ ID NO 1
<211> LENGTH: 103
<212> TYPE: PRT
<213> ORGANISM: Escherichia coli

<400> SEQUENCE: 1

Ala Pro Gln Ser Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100


<210> SEQ ID NO 2
<211> LENGTH: 61
<212> TYPE: PRT
<213> ORGANISM: Escherichia coli

<400> SEQUENCE: 2

Ala Pro Gln Ser Ile Thr Glu Leu Cys Ser Glu Tyr Arg Asn Thr Gln
1               5                   10                  15
```

```
Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Ala Thr Phe
        35                  40                  45

Gln Val Glu Val Pro Gly Ser Gln His Ile Asp Ser Gln
    50                  55                  60


<210> SEQ ID NO 3
<211> LENGTH: 42
<212> TYPE: PRT
<213> ORGANISM: Escherichia coli

<400> SEQUENCE: 3

Lys Lys Ala Ile Glu Arg Met Lys Asp Thr Leu Arg Ile Thr Tyr Leu
1               5                   10                  15

Thr Glu Thr Lys Ile Asp Lys Leu Cys Val Trp Asn Asn Lys Thr Pro
            20                  25                  30

Asn Ser Ile Ala Ala Ile Ser Met Glu Asn
        35                  40


<210> SEQ ID NO 4
<211> LENGTH: 240
<212> TYPE: PRT
<213> ORGANISM: Escherichia coli

<400> SEQUENCE: 4

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240
```

<210> SEQ ID NO 5
<211> LENGTH: 60
<212> TYPE: PRT
<213> ORGANISM: Escherichia coli

<400> SEQUENCE: 5

```
Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val
    50                  55                  60
```

<210> SEQ ID NO 6
<211> LENGTH: 60
<212> TYPE: PRT
<213> ORGANISM: Escherichia coli

<400> SEQUENCE: 6

```
Ser Thr Ser Leu Ser Leu Arg Ser Ala His Leu Ala Gly Gln Ser Ile
1               5                   10                  15

Leu Ser Gly Tyr Ser Thr Tyr Tyr Ile Tyr Val Ile Ala Thr Ala Pro
            20                  25                  30

Asn Met Phe Asn Val Asn Asp Val Leu Gly Val Tyr Ser Pro His Pro
        35                  40                  45

Tyr Glu Gln Glu Val Ser Ala Leu Gly Gly Ile Pro
    50                  55                  60
```

<210> SEQ ID NO 7
<211> LENGTH: 60
<212> TYPE: PRT
<213> ORGANISM: Escherichia coli

<400> SEQUENCE: 7

```
Tyr Ser Gln Ile Tyr Gly Trp Tyr Arg Val Asn Phe Gly Val Ile Asp
1               5                   10                  15

Glu Arg Leu His Arg Asn Arg Glu Tyr Arg Asp Arg Tyr Tyr Arg Asn
            20                  25                  30

Leu Asn Ile Ala Pro Ala Glu Asp Gly Tyr Arg Leu Ala Gly Phe Pro
        35                  40                  45

Pro Asp His Gln Ala Trp Arg Glu Glu Pro Trp Ile
    50                  55                  60
```

<210> SEQ ID NO 8
<211> LENGTH: 60
<212> TYPE: PRT
<213> ORGANISM: Escherichia coli

<400> SEQUENCE: 8

```
His His Ala Pro Gln Gly Cys Gly Asn Ser Ser Arg Thr Ile Thr Gly
1               5                   10                  15

Asp Thr Cys Asn Glu Glu Thr Gln Asn Leu Ser Thr Ile Tyr Leu Arg
            20                  25                  30

Lys Tyr Gln Ser Lys Val Lys Arg Gln Ile Phe Ser Asp Tyr Gln Ser
        35                  40                  45

Glu Val Asp Ile Tyr Asn Arg Ile Arg Asn Glu Leu
    50                  55                  60
```

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120
```

<210> SEQ ID NO 10
<211> LENGTH: 1275
<212> TYPE: PRT
<213> ORGANISM: Escherichia coli

<400> SEQUENCE: 10

```
Met Gln Phe Ile Thr Asn Gly Pro Asp Ile Pro Asp Glu Phe Leu Gln
1               5                   10                  15

Ala His Glu Glu Gly Arg Val Val Phe Phe Cys Gly Ala Gly Ile Ser
            20                  25                  30

Tyr Pro Ala Gly Leu Pro Gly Phe Lys Gly Leu Val Glu Leu Ile Tyr
        35                  40                  45

Gln Arg Asn Gly Thr Thr Leu Ser Glu Ile Glu Arg Glu Val Phe Glu
    50                  55                  60

Arg Gly Gln Phe Asp Gly Thr Leu Asp Leu Leu Glu Arg Arg Leu Pro
65                  70                  75                  80

Gly Gln Arg Ile Ala Val Arg Arg Ala Leu Glu Lys Ala Leu Lys Pro
                85                  90                  95

Lys Leu Arg Arg Arg Gly Ala Ile Asp Thr Gln Ala Ala Leu Leu Arg
            100                 105                 110

Leu Ala Arg Ser Arg Glu Gly Ala Leu Arg Leu Val Thr Thr Asn Phe
        115                 120                 125

Asp Arg Leu Phe His Val Ala Ala Lys Arg Thr Gly Gln Ala Phe Gln
    130                 135                 140

Ala Tyr Val Ala Pro Met Leu Pro Ile Pro Lys Asn Ser Arg Trp Asp
145                 150                 155                 160

Gly Leu Val Tyr Leu His Gly Leu Leu Pro Glu Lys Ala Asp Asp Thr
                165                 170                 175

Ala Leu Asn Arg Leu Val Val Thr Ser Gly Asp Phe Gly Leu Ala Tyr
            180                 185                 190
```

-continued

```
Leu Thr Glu Arg Trp Ala Ala Arg Phe Val Ser Glu Leu Phe Arg Asn
        195                 200                 205

Tyr Val Val Cys Phe Val Gly Tyr Ser Ile Asn Asp Pro Val Leu Arg
    210                 215                 220

Tyr Met Met Asp Ala Leu Ala Ala Asp Arg Arg Leu Gly Glu Val Thr
225                 230                 235                 240

Pro Gln Val Trp Ala Leu Gly Glu Cys Glu Pro Gly Gln Glu His Arg
                245                 250                 255

Lys Ala Ile Glu Trp Glu Ala Lys Gly Val Thr Pro Ile Leu Tyr Thr
            260                 265                 270

Val Pro Ala Gly Ser Thr Asp His Ser Val Leu His Gln Thr Leu His
        275                 280                 285

Ala Trp Ala Asp Thr Tyr Arg Asp Gly Ile Gln Gly Lys Lys Ala Ile
    290                 295                 300

Val Val Lys His Ala Leu Ala Arg Pro Gln Asp Ser Thr Arg Gln Asp
305                 310                 315                 320

Asp Phe Val Gly Arg Met Leu Trp Ala Leu Ser Asp Lys Ser Gly Leu
                325                 330                 335

Pro Ala Lys Arg Phe Ala Glu Leu Asn Pro Ala Pro Pro Leu Asp Trp
            340                 345                 350

Leu Leu Lys Ala Phe Ser Asp Glu Arg Phe Lys Tyr Ser Asp Leu Pro
        355                 360                 365

Arg Phe Cys Val Ser Pro His Val Glu Ile Asp Pro Lys Leu Arg Phe
    370                 375                 380

Ser Leu Val Gln Arg Pro Ala Pro Tyr Glu Leu Ala Pro Gln Met Ser
385                 390                 395                 400

Leu Val Ser Gly Cys Val Ser Ala Ser Lys Trp Asp Asp Val Met Ser
                405                 410                 415

His Ile Ala Arg Trp Leu Val Arg Tyr Leu Gly Asp Pro Arg Leu Ile
            420                 425                 430

Ile Trp Ile Ala Glu Arg Gly Gly Gln Ile His Asp Arg Trp Met Phe
        435                 440                 445

Leu Ile Glu Ser Glu Leu Asp Arg Leu Ala Ala Leu Met Arg Glu Arg
    450                 455                 460

Lys Thr Ser Glu Leu Asp Glu Ile Leu Leu His Ser Pro Leu Ala Ile
465                 470                 475                 480

Pro Gly Pro Pro Met Ser Thr Leu Trp Arg Leu Leu Leu Ser Gly Arg
                485                 490                 495

Val Lys Ser Pro Leu Gln Asn Leu Asp Leu Tyr Arg Trp Gln Asn Arg
            500                 505                 510

Leu Lys Asn Glu Gly Leu Thr Thr Thr Leu Arg Leu Glu Leu Arg Gly
        515                 520                 525

Leu Leu Ser Pro Lys Val Met Leu Arg Arg Pro Phe Arg Tyr Ser Glu
    530                 535                 540

Asp Asp Ser Ser Ser Thr Asp Glu Pro Leu Arg Ile Lys Gln Leu Val
545                 550                 555                 560

Asp Trp Glu Leu Val Leu Thr Ala Asp Tyr Val Arg Ser Thr Leu Phe
                565                 570                 575

Asp Leu Ala Asp Glu Ser Trp Lys Ser Ser Leu Pro Tyr Leu Leu Glu
            580                 585                 590

Asp Phe Gln Gln Leu Leu Arg Asp Ala Leu Asp Leu Leu Arg Glu Leu
        595                 600                 605
```

-continued

```
Gly Glu Ser Asp Asp Arg His Asp Arg Ser His Trp Asp Leu Pro Ser
    610                 615                 620

Ile Thr Pro His Trp Gln Asn Arg Gly Phe Arg Asp Trp Val Ser Leu
625                 630                 635                 640

Ile Glu Leu Leu Arg Asp Ser Trp Leu Ala Val Arg Ala Lys Asp Ser
                645                 650                 655

Asp Gln Ala Ser Arg Ile Ala Gln Asn Trp Phe Glu Leu Pro Tyr Pro
            660                 665                 670

Thr Phe Lys Arg Leu Ala Leu Phe Ala Ala Ser Gln Asp Asn Cys Ile
        675                 680                 685

Pro Pro Glu Arg Trp Val Asn Trp Leu Leu Glu Asp Gly Ser Trp Trp
    690                 695                 700

Leu Trp Ala Thr Asp Thr Arg Arg Glu Val Phe Arg Leu Phe Val Leu
705                 710                 715                 720

Gln Gly Arg His Leu Thr Gly Ile Ala Gln Glu Arg Leu Glu Thr Ala
                725                 730                 735

Ile Leu Ala Gly Pro Pro Arg Glu Met Tyr Glu Asp Asn Leu Glu Ala
            740                 745                 750

Asp Arg Trp His Tyr Leu Val Ala His Ser Val Trp Leu Cys Leu Ala
        755                 760                 765

Lys Leu Arg Gly Ala Gly Leu Val Leu Gly Glu Ser Ala Ala Thr Arg
    770                 775                 780

Leu Thr Glu Ile Ser Thr Ala Tyr Pro Lys Trp Gln Leu Ala Thr Asn
785                 790                 795                 800

Glu Arg Asp Glu Phe Ser His Trp Met Ser Gly Thr Gly Asp Pro Gly
                805                 810                 815

Phe Glu Glu Ser Ile Asp Val Asp Ile Ala Pro Arg Lys Trp Gln Glu
            820                 825                 830

Leu Val Gln Trp Leu Ala Lys Pro Met Pro Glu Arg Leu Pro Phe Tyr
        835                 840                 845

Glu Asp Thr Trp Ser Asp Val Cys Arg Thr Arg Phe Phe His Ser Leu
    850                 855                 860

Tyr Ala Leu Arg Lys Leu Ser Gln Asp Asp Val Trp Pro Val Gly Arg
865                 870                 875                 880

Trp Arg Glu Ala Leu Gln Thr Trp Ala Glu Pro Gly Met Ile Leu Arg
                885                 890                 895

Ser Trp Arg Tyr Ala Ala Pro Leu Val Leu Asp Met Pro Asp Ala Val
            900                 905                 910

Leu Gln Glu Ile Ser His Ala Val Thr Trp Trp Met Glu Glu Ala Ser
        915                 920                 925

Lys Thr Ile Leu Cys His Glu Glu Ile Leu Leu Ala Leu Cys Arg Arg
    930                 935                 940

Val Leu Met Ile Glu Thr Ser Pro Glu Ser Ser Thr Ile Arg Asn Gly
945                 950                 955                 960

Ile Glu Thr Tyr Asp Pro Val Ser Thr Ala Ile Asn His Pro Ile Gly
                965                 970                 975

His Val Thr Gln Ser Leu Ile Thr Leu Trp Phe Lys Gln Asn Pro Asn
            980                 985                 990

Asp Asn Asp Leu Leu Pro Val Glu  Leu Lys Thr Leu Phe  Thr Lys Leu
        995                 1000                1005

Cys Asn  Val Gln Ile Glu Leu  Phe Arg His Gly Arg  Val Leu Leu
    1010                1015                1020

Gly Ser  Arg Leu Ile Ala Phe  Phe Arg Val Asp Arg  Pro Trp Thr
```

```
    1025                1030                1035

Glu Gln  Tyr Leu Leu Pro Leu  Phe Ala Trp Ser Asn  Pro Val Glu
    1040                1045                1050

Ala Lys  Ala Val Trp Glu Gly  Phe Leu Trp Ser Pro  Arg Leu Tyr
    1055                1060                1065

Glu Pro  Leu Leu Ile Ala Phe  Lys Ser Asp Phe Leu  Glu Ser Ala
    1070                1075                1080

Asn His  Tyr Ser Asp Leu Gly  Glu His Arg Gln Gln  Phe Ala Ile
    1085                1090                1095

Phe Leu  Thr Tyr Ala Ala Leu  Gly Pro Thr Glu Gly  Tyr Thr Val
    1100                1105                1110

Glu Glu  Phe Arg Thr Ala Ile  Ser Ala Leu Pro Gln  Glu Gly Leu
    1115                1120                1125

Glu Val  Ala Ala Gln Ala Leu  Tyr Gln Ala Leu Glu  Gly Ala Gly
    1130                1135                1140

Asp Gln  Arg Glu Glu Tyr Trp  Lys Asn Arg Val Gln  Pro Phe Trp
    1145                1150                1155

Gln Gln  Val Trp Pro Lys Ser  Arg Asn Leu Ala Thr  Pro Arg Ile
    1160                1165                1170

Ser Glu  Ser Leu Thr Arg Met  Val Ile Ala Ala Arg  Gly Glu Phe
    1175                1180                1185

Pro Ala  Ala Leu Ala Val Val  Gln Asp Trp Leu Gln  Pro Leu Glu
    1190                1195                1200

His Leu  Ser Tyr Asp Val Arg  Leu Leu Leu Glu Ser  Asp Ile Cys
    1205                1210                1215

Ser Arg  Tyr Pro Ala Asp Ala  Leu Ser Leu Leu Asn  Ala Val Ile
    1220                1225                1230

Ala Glu  Gln His Trp Gly Pro  Arg Glu Leu Gly Gln  Cys Leu Leu
    1235                1240                1245

Gln Ile  Val Gln Ala Ala Pro  Gln Leu Glu Gln Asp  Val Arg Tyr
    1250                1255                1260

Gln Arg  Leu Asn Glu Tyr Ser  Arg Arg Arg Ser Val
    1265                1270                1275


<210> SEQ ID NO 11
<211> LENGTH: 1275
<212> TYPE: PRT
<213> ORGANISM: Escherichia coli

<400> SEQUENCE: 11

Met Gln Phe Ile Thr Asn Gly Pro Asp Ile Pro Asp Glu Phe Leu Gln
1               5                   10                  15

Ala His Glu Glu Gly Arg Val Val Phe Phe Cys Gly Ala Gly Ile Ser
            20                  25                  30

Tyr Pro Ala Gly Leu Pro Gly Phe Lys Gly Leu Val Glu Leu Ile Tyr
        35                  40                  45

Gln Arg Asn Gly Thr Thr Leu Ser Glu Ile Glu Arg Glu Val Phe Glu
    50                  55                  60

Arg Gly Gln Phe Asp Gly Thr Leu Asp Leu Leu Glu Arg Arg Leu Pro
65                  70                  75                  80

Gly Gln Arg Ile Ala Val Arg Arg Ala Leu Glu Lys Ala Leu Lys Pro
                85                  90                  95

Lys Leu Arg Arg Arg Gly Ala Ile Asp Thr Gln Ala Ala Leu Leu Arg
            100                 105                 110
```

-continued

```
Leu Ala Arg Ser Arg Glu Gly Ala Leu Arg Leu Val Thr Thr Asn Phe
        115                 120                 125

Asp Arg Leu Phe His Val Ala Ala Lys Arg Thr Gly Gln Ala Phe Gln
    130                 135                 140

Ala Tyr Val Ala Pro Met Leu Pro Ile Pro Lys Asn Ser Arg Trp Asp
145                 150                 155                 160

Gly Leu Val Tyr Leu His Gly Leu Leu Pro Glu Lys Ala Asp Asp Thr
                165                 170                 175

Ala Leu Asn Arg Leu Val Val Thr Ser Gly Asp Phe Gly Leu Ala Tyr
            180                 185                 190

Leu Thr Glu Arg Trp Ala Ala Arg Phe Val Ser Glu Leu Phe Arg Asn
        195                 200                 205

Tyr Val Val Cys Phe Val Gly Tyr Ser Ile Asn Asp Pro Val Leu Arg
    210                 215                 220

Tyr Met Met Asp Ala Leu Ala Ala Asp Arg Arg Leu Gly Glu Val Thr
225                 230                 235                 240

Pro Gln Val Trp Ala Leu Gly Glu Cys Glu Pro Gly Gln Glu His Arg
                245                 250                 255

Lys Ala Ile Glu Trp Glu Ala Lys Gly Val Thr Pro Ile Leu Tyr Thr
            260                 265                 270

Val Pro Ala Gly Ser Thr Asp His Ser Val Leu His Gln Thr Leu His
        275                 280                 285

Ala Trp Ala Asp Thr Tyr Arg Asp Gly Ile Gln Gly Lys Lys Ala Ile
    290                 295                 300

Val Val Lys His Ala Leu Ala Arg Pro Gln Asp Ser Thr Arg Gln Asp
305                 310                 315                 320

Asp Phe Val Gly Arg Met Leu Trp Ala Leu Ser Asp Lys Ser Gly Leu
                325                 330                 335

Pro Ala Lys Arg Phe Ala Glu Leu Asn Pro Ala Pro Pro Leu Asp Trp
            340                 345                 350

Leu Leu Lys Ala Phe Ser Asp Glu Arg Phe Lys Tyr Ser Asp Leu Pro
        355                 360                 365

Arg Phe Cys Val Ser Pro His Val Glu Ile Asp Pro Lys Leu Arg Phe
    370                 375                 380

Ser Leu Val Gln Arg Pro Ala Pro Tyr Glu Leu Ala Pro Gln Met Ser
385                 390                 395                 400

Leu Val Ser Gly Cys Val Ser Ala Ser Lys Trp Asp Asp Val Met Ser
                405                 410                 415

His Ile Ala Arg Trp Leu Val Arg Tyr Leu Gly Asp Pro Arg Leu Ile
            420                 425                 430

Ile Trp Ile Ala Glu Arg Gly Gly Gln Ile His Asp Arg Trp Met Phe
        435                 440                 445

Leu Ile Glu Ser Glu Leu Asp Arg Leu Ala Ala Leu Met Arg Glu Arg
    450                 455                 460

Lys Thr Ser Glu Leu Asp Glu Ile Leu Leu His Ser Pro Leu Ala Ile
465                 470                 475                 480

Pro Gly Pro Pro Met Ser Thr Leu Trp Arg Leu Leu Leu Ser Gly Arg
                485                 490                 495

Val Lys Ser Pro Leu Gln Asn Leu Asp Leu Tyr Arg Trp Gln Asn Arg
            500                 505                 510

Leu Lys Asn Glu Gly Leu Thr Thr Thr Leu Arg Leu Glu Leu Arg Gly
        515                 520                 525

Leu Leu Ser Pro Lys Val Met Leu Arg Arg Pro Phe Arg Tyr Ser Glu
```

```
    530                 535                 540

Asp Asp Ser Ser Ser Thr Asp Glu Pro Leu Arg Ile Lys Gln Leu Val
545                 550                 555                 560

Asp Trp Glu Leu Val Leu Thr Ala Asp Tyr Val Arg Ser Thr Leu Phe
                565                 570                 575

Asp Leu Ala Asp Glu Ser Trp Lys Ser Ser Leu Pro Tyr Leu Leu Glu
            580                 585                 590

Asp Phe Gln Gln Leu Leu Arg Asp Ala Leu Asp Leu Leu Arg Glu Leu
        595                 600                 605

Gly Glu Ser Asp Asp Arg His Asp Arg Ser His Trp Asp Leu Pro Ser
    610                 615                 620

Ile Thr Pro His Trp Gln Asn Arg Gly Phe Arg Asp Trp Val Ser Leu
625                 630                 635                 640

Ile Glu Leu Leu Arg Asp Ser Trp Leu Ala Val Arg Ala Lys Asp Ser
                645                 650                 655

Asp Gln Ala Ser Arg Ile Ala Gln Asn Trp Phe Glu Leu Pro Tyr Pro
            660                 665                 670

Thr Phe Lys Arg Leu Ala Leu Phe Ala Ala Ser Gln Asp Asn Cys Ile
        675                 680                 685

Pro Pro Glu Arg Trp Val Asn Trp Leu Leu Glu Asp Gly Ser Trp Trp
    690                 695                 700

Leu Trp Ala Thr Asp Thr Arg Arg Glu Val Phe Arg Leu Phe Val Leu
705                 710                 715                 720

Gln Gly Arg His Leu Thr Gly Ile Ala Gln Glu Arg Leu Glu Thr Ala
                725                 730                 735

Ile Leu Ala Gly Pro Pro Arg Glu Met Tyr Glu Asp Asn Leu Glu Ala
            740                 745                 750

Asp Arg Trp His Tyr Leu Val Ala His Ser Val Trp Leu Cys Leu Ala
        755                 760                 765

Lys Leu Arg Gly Ala Gly Leu Val Leu Gly Glu Ser Ala Ala Thr Arg
    770                 775                 780

Leu Thr Glu Ile Ser Thr Ala Tyr Pro Lys Trp Gln Leu Ala Thr Asn
785                 790                 795                 800

Glu Arg Asp Glu Phe Ser His Trp Met Ser Gly Thr Gly Asp Pro Gly
                805                 810                 815

Phe Glu Glu Ser Ile Asp Val Asp Ile Ala Pro Arg Lys Trp Gln Glu
            820                 825                 830

Leu Val Gln Trp Leu Ala Lys Pro Met Pro Glu Arg Leu Pro Phe Tyr
        835                 840                 845

Glu Asp Thr Trp Ser Asp Val Cys Arg Thr Arg Phe Phe His Ser Leu
    850                 855                 860

Tyr Ala Leu Arg Lys Leu Ser Gln Asp Asp Val Trp Pro Val Gly Arg
865                 870                 875                 880

Trp Arg Glu Ala Leu Gln Thr Trp Ala Glu Pro Gly Met Ile Leu Arg
                885                 890                 895

Ser Trp Arg Tyr Ala Ala Pro Leu Val Leu Asp Met Pro Asp Ala Val
            900                 905                 910

Leu Gln Glu Ile Ser His Ala Val Thr Trp Trp Met Glu Glu Ala Ser
        915                 920                 925

Lys Thr Ile Leu Cys His Glu Glu Ile Leu Leu Ala Leu Cys Arg Arg
    930                 935                 940

Val Leu Met Ile Glu Thr Ser Pro Glu Ser Ser Thr Ile Arg Asn Gly
945                 950                 955                 960
```

```
Ile Glu Thr Tyr Asp Pro Val Ser Thr Ala Ile Asn His Pro Ile Gly
                965                 970                 975

His Val Thr Gln Ser Leu Ile Thr Leu Trp Phe Lys Gln Asn Pro Asn
            980                 985                 990

Asp Asn Asp Leu Leu Pro Val Glu  Leu Lys Thr Leu Phe  Thr Lys Leu
        995                 1000                1005

Cys Asn  Val Gln Ile Glu Leu  Phe Arg His Gly Arg  Val Leu Leu
    1010                 1015                1020

Gly Ser  Arg Leu Ile Ala Phe  Phe Arg Val Asp Arg  Pro Trp Thr
    1025                 1030                1035

Glu Gln  Tyr Leu Leu Pro Leu  Phe Ala Trp Ser Asn  Pro Val Glu
    1040                 1045                1050

Ala Lys  Ala Val Trp Glu Gly  Phe Leu Trp Ser Pro  Arg Leu Tyr
    1055                 1060                1065

Glu Pro  Leu Leu Ile Ala Phe  Lys Ser Asp Phe Leu  Glu Ser Ala
    1070                 1075                1080

Asn His  Tyr Ser Asp Leu Gly  Glu His Arg Gln Gln  Phe Ala Ile
    1085                 1090                1095

Phe Leu  Thr Tyr Ala Ala Leu  Gly Pro Thr Glu Gly  Tyr Thr Val
    1100                 1105                1110

Glu Glu  Phe Arg Thr Ala Ile  Ser Ala Leu Pro Gln  Glu Gly Leu
    1115                 1120                1125

Glu Val  Ala Ala Gln Ala Leu  Tyr Gln Ala Leu Glu  Gly Ala Gly
    1130                 1135                1140

Asp Gln  Arg Glu Glu Tyr Trp  Lys Asn Arg Val Gln  Pro Phe Trp
    1145                 1150                1155

Gln Gln  Val Trp Pro Lys Ser  Arg Asn Leu Ala Thr  Pro Arg Ile
    1160                 1165                1170

Ser Glu  Ser Leu Thr Arg Met  Val Ile Ala Ala Arg  Gly Glu Phe
    1175                 1180                1185

Pro Ala  Ala Leu Ala Val Val  Gln Asp Trp Leu Gln  Pro Leu Glu
    1190                 1195                1200

His Leu  Ser Tyr Asp Val Arg  Leu Leu Leu Glu Ser  Asp Ile Cys
    1205                 1210                1215

Ser Arg  Tyr Pro Ala Asp Ala  Leu Ser Leu Leu Asn  Ala Val Ile
    1220                 1225                1230

Ala Glu  Gln His Trp Gly Pro  Arg Glu Leu Gly Gln  Cys Leu Leu
    1235                 1240                1245

Gln Ile  Val Gln Ala Ala Pro  Gln Leu Glu Gln Asp  Val Arg Tyr
    1250                 1255                1260

Gln Arg  Leu Asn Glu Tyr Ser  Arg Arg Arg Ser Val
    1265                 1270                1275
```

<210> SEQ ID NO 12
<211> LENGTH: 149
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Asn Lys Val Lys Cys Tyr Val Leu Phe Thr Ala Leu Leu Ser Ser
1               5                   10                  15

Leu Cys Ala Tyr Gly Ala Pro Gln Ser Ile Thr Glu Leu Cys Ser Glu
```

-continued

```
        20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Leu Gln Asn Leu Asp Leu Tyr Arg Trp Gln Asn Arg Leu Lys Asn Glu
                85                  90                  95

Gly Leu Thr Thr Thr Leu Arg Leu Glu Ser Gln Lys Lys Ala Ile Glu
            100                 105                 110

Arg Met Lys Asp Thr Leu Arg Ile Thr Tyr Leu Thr Glu Thr Lys Ile
        115                 120                 125

Asp Lys Leu Cys Val Trp Asn Asn Lys Thr Pro Asn Ser Ile Ala Ala
    130                 135                 140

Ile Ser Met Glu Asn
145


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5


<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

tttttttttt tttttttt                                                18
```